United States Patent [19]

Molaire

[11] Patent Number: 4,626,361

[45] Date of Patent: Dec. 2, 1986

[54] BINDER-MIXTURES FOR OPTICAL RECORDING LAYERS AND ELEMENTS

[75] Inventor: Michel F. Molaire, Rochester, N.Y.

[73] Assignee: Eastman Kodak Company, Rochester, N.Y.

[21] Appl. No.: 662,920

[22] Filed: Oct. 19, 1984

Related U.S. Application Data

[62] Division of Ser. No. 473,825, Mar. 9, 1983, Pat. No. 4,499,165.

[51] Int. Cl.$^4$ .............................................. C09K 3/00
[52] U.S. Cl. ..................................... 252/1; 252/582; 346/76 L; 346/135.1; 430/270; 430/271; 430/346; 430/495; 430/908; 430/945
[58] Field of Search ............... 430/495, 945, 346, 270, 430/271, 908, 33; 346/135.1, 76 L

[56] References Cited

U.S. PATENT DOCUMENTS

| | | | |
|---|---|---|---|
| 3,607,261 | 9/1971 | Amido et al. | 430/76 |
| 4,032,691 | 6/1977 | Kido et al. | 346/76 L |
| 4,150,985 | 4/1979 | Shattuck | 430/33 |
| 4,230,939 | 10/1980 | deBont et al. | 346/135.1 |
| 4,270,130 | 5/1981 | Houle et al. | 346/135.1 |
| 4,284,699 | 8/1981 | Berwick et al. | 430/96 |
| 4,320,489 | 3/1982 | Crandall et al. | 346/135.1 |
| 4,322,490 | 3/1982 | Molaire | 430/281 |
| 4,340,454 | 7/1982 | Martin et al. | 204/159.19 |
| 4,364,986 | 12/1982 | Zwanerburg et al. | 430/945 |
| 4,380,769 | 4/1983 | Thomas et al. | 346/135.1 |
| 4,416,965 | 11/1983 | Sandhu | 430/109 |
| 4,419,437 | 12/1983 | Noonan et al. | 430/270 |

*Primary Examiner*—Charles L. Bowers, Jr.
*Attorney, Agent, or Firm*—John R. Everett

[57] ABSTRACT

A solid, nonpolymeric amorphous mixture of compounds which is useful as a binder in optical recording layers and elements is disclosed. The mixture comprises at least two different compounds each having at least two linking components joining one multivalent organic nucleus with at least two organic nuclei wherein at least one of the multivalent organic nucleus and the organic nuclei is multicyclic. Methods for making such mixtures are also disclosed.

7 Claims, No Drawings

BINDER-MIXTURES FOR OPTICAL RECORDING LAYERS AND ELEMENTS

This is a division of application Ser. No. 473,825, filed Mar. 9, 1983, now U.S. Pat. No. 4,499,165.

FIELD OF THE INVENTION

The present invention relates to mixtures of compounds, methods for making such mixtures and the use of such mixtures as binders in optical recording layers and elements.

BACKGROUND OF THE INVENTION

In optical recording processes generally a laser beam is modulated, e.g., pulsed corresponding to a pattern of information, and focused onto the surface of a recording layer of a recording element.

The recording layer absorbs sufficient energy at the wavelength of the laser beam to cause small portions of the layer to burn, evaporate or otherwise be deformed. Generally, there is continuous relative motion between the laser and the layer so that, as the laser is pulsed or modulated, discrete pits or holes of varying sizes are created in the layer. The sizes and spacings of these holes constitute the encoded information.

The resulting recorded information element is generally read back by turning down the power of the writing laser or by using another laser to which the layer is transparent, thereby precluding the reading laser from further physically altering the recorded layer. The reading beam is disposed to follow the same path as the recording beam. When the read beam is significantly absorbed by the recording, an optical density difference is detected between pits and unrecorded areas. When the read beam is transmitted by the layer, light scattering caused by the pits and unrecorded areas are detected as an optical density difference.

This density difference is detected by a photodetector positioned to receive laser radiation reflected from the underlying support (in the case of a reflective support) or positioned to receive laser radiation transmitted through the underlying support where holes have been formed in the recording layer (in the case of a transmissive support). The detected density variations are converted back into electrical signals corresponding to the information recorded.

In one type of known recording element, the recording layer comprises a mixture of a binder and dye. The dye has an absorption maximum at or near the wavelength of the laser beam used to thermally deform the recording layer. Known binders include polymer or plastic materials such as cellulose nitrate, cellulose butyrates, polycarbonates, polystyrenes and various rosin derivatives.

In order to be useful in optical recording elements, the binder must be compatible with the selected dye. That is, the binder must be capable of forming an amorphous mixture with the dye at high dye to binder ratios and the amorphous mixture should exhibit a single thermal transition with no phase separation, such as crystallization of the dye or polymer, after annealing. It is also desirable that the binder have (a) a relatively low melt viscosity to facilitate rapid formation of the laser induced deformations, and (b) a relatively high glass transition temperature (Tg) to retain the shape of the deformations after formation thereof.

None of the above mentioned known binders are completely satisfactory. The most frequently used material, cellulose nitrate, is unstable and under certain conditions explosive. Also, recording layers containing cellulose nitrate tend to lose considerable absorption at temperatures above room temperature. Cellulose nitrate also has limited compatibility with certain classes of useful dyes such as infrared absorbing metal dithiene dyes.

SUMMARY OF THE INVENTION

The present invention provides a novel mixture of non-polymeric compounds which is useful as the binder in layers of recording and recorded information elements. The mixture of compounds (sometimes referred to hereinafter as binder-mixture) are more compatible with a wide variety of dyes including infrared absorbing metal dithiene dyes compared to cellulose nitrate. The absorption of compositions containing the mixtures with a dye has greatly improved stability compared with that of such compositions containing cellulose nitrate. Moreover, the mixtures are not explosive.

The mixture of compounds useful as binders is characterized in that the mixture is (a) amorphous (b) is solid at about 20° C. and (c) comprises at least two different compounds each having at least two linking components joining one multivalent organic nucleus with at least two organic nuclei wherein at least one of the multivalent organic nucleus and the organic nuclei is a multicyclic aromatic nucleus.

DESCRIPTION OF THE PREFERRED EMBODIMENTS

Preferred mixtures contain at least two different compounds each having the structure

wherein
m is zero or one;
n is the number of recurring units in the compound, and is zero up to, but not including, an integer at which said compound starts to become a polymer;
p is an integer of from one to eight;
Each $R^1$ and $R^3$ is independently a monovalent aliphatic or cyloaliphatic hydrocarbon group having 1 to 20 carbon atoms, an aromatic group or a multicyclic aromatic nucleus;
$R^2$, $Z^1$ and $Z^2$ each independently represent multivalent aliphatic or cycloaliphatic hydrocarbon groups having 1 to 20 carbon atoms or an aromatic group;
$Y^1$, $Y^2$, $Y^3$ and $Y^4$ each independently represents one or more linking groups such as esters (—COO—), amides (—CONH—), imides

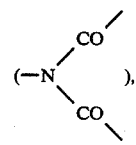

urethanes (—NHCOO—), nitrilomethyl eneoxys

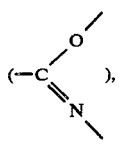

nitrilomethyleneiminos

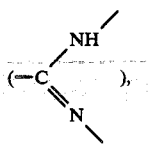

nitrilomethylenethios

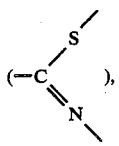

1,3,4-triazol-2,5-ylenes

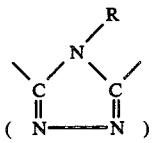

wherein R represents alkyl of 1–6 carbon atoms, hydroxyl, amino and aryl such as phenyl and 1,3,4-oxadiazol-2,5-ylenes

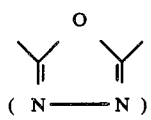

provided that at least one of $R^1$, $Z^1$, $R^2$, $R^3$ and $Z^2$ is a multicyclic aromatic nucleus.

In the structural formula, the expression "$[(Z^1Y^2)_m\text{-}R^2Y^3]_n$," describes nonpolymeric compounds which are oligomers. Oligomers are usually formed when either $Z^1$ or $R^2$ are at least bivalent. The $(Z^1Y^2)_m$ moiety describes oligomers in which $Z^1$ repeats itself such as when $Z^1$ is derived from p-hydroxybenzoic acid. When n is one or more, p in the structural formula is preferably one to avoid significant crosslinking of the compound due to the multivalent nature of $Z^1$. However, some crosslinking can be tolerated in binder-mixtures for optical recording elements.

The term "amorphous" means that the mixture is noncrystalline. That is, the mixture has no molecular lattice structure.

A "multicyclic aromatic nucleus" is a nucleus comprising at least two cyclic groups one of which is aromatic, including aromatic heterocyclic ring groups. The cyclic group may be substituted with substituents such as aliphatic hydrocarbons, including cycloaliphatic hydrocarbons, other aromatic ring groups such as aryl, and heterocyclic ring groups such as substituted or fused thiazole, oxazole, imide, pyrazole, triazole, oxadiazole, pyridine, pyrimidine, pyrazine, triazine, tetrazine and quinoline groups. The substituents are fused or non-fused and mono or polycyclic. Examples of multicyclic aromatic nuclei include 9,9-bis(4-hydroxy-3,5-dichlorophenyl)fluorene, 4,4'-hexahydro-4,7-methanoindan-5-ylidenebis(2,6-dichlorophenol); 9,9-bis(4-hydroxy-3,5-dibromophenyl-(fluorene, 4,4'-hexahydro-4,7-methanoindan-5-ylidenebis(2,6-dibromophenol); 3',3",5',5"-tetrabromophenolphthalein, 9,9-bis(4-aminophenyl)-fluorene, phenylindandiols; 1,1'-spirobiindandiols, 1,1'-spirobiindandiamines, 2,2'spirobichromans; 7,7-dimethyl-7H-dibenzo[c,h]xanthenediol; xanthylium salts diols; 9,9-dimethylxanthene-3,6-bis(oxyacetic acids); 4,4'(3-phenyl-1-indanylidene)-diphenol and other bisphenols; 3',3"-dibromo-5',5"-dinitro-2',2"-oxaphenolphthalein; 9-phenyl-3-oxo-2,6,7-trihydroxyxanthene; and the like.

"Aliphatic hydrocarbon group" refers to monovalent or divalent, alkanes, alkenes, alkadienes and alkynes having from 1 to 20 carbon atoms. The groups are straight or branched chain and include carbohydrate, carboxylic acid, alcohol, ether aldehyde and ketone functions. "Cycloaliphatic" refers to cyclic aliphatic hydrocarbon groups. The groups may be substituted with halogen, alkoxy, amide, nitro, esters and aromatic groups.

Exemplary aliphatic groups include methyl, ethyl, propyl, isopropyl, butyl, hexyl, 2-ethylhexyl, methoxyethyl, ethoxycarbonylpropyl, 3-oxobutyl, 3-thiapentyl, furfuryl, 2-thiazolylmethyl, cyclohexylmethyl, benzyl, phenethyl, phenoxyethyl, vinyl(—CH=CH—), 2-methylvinyl, allyl, allylidene, butadienyl, butenylidene, propargyl, etc.

"Aromatic" and "aromatic heterocyclic" group refers to organic groups which undergo the same type of substitution reaction as benzene. In benzene, substitution reactions are preferred over addition reactions. Such groups preferably have from 6 to about 40 nuclear atoms and are mono- and polycyclic.

Exemplary aromatic groups include quinolinyl, pyrimidinyl, pyridyl, phenyl, tolyl, xylyl, naphthyl, anthryl, triptycenyl, p-chlorophenyl, p-nitrophenyl, p-bromophenyl, 2,4-dichlorophenyl, 2-chlorophenyl, 3,5-dinitrophenyl, p-(tetrabromophthalimido)phenyl, p-(tetrachlorophthalimido)phenyl, p-tetraphenylphthalimido)phenyl, p-naphthalimidophenyl, p-(4-nitrophthalimido)phenyl,p-phthalimidophenyl, 1-hydroxy-2-naphthyl, 3,5-dibromo-4-(4-bromobenzoyloxy)phenyl, 3,5-dibromo-4-(3,5-dinitrobenzoyloxy)phenyl, 3,5-dibromo-4-(1-naphthoyloxy)phenyl, thiazolyl, oxazolyl, imidazolyl, pyrazolyl, triazolyl, oxadiazolyl, pyrazinyl, etc and their corresponding multivalent and fused ring configurations.

Although the compounds in the mixture are nonpolymeric, compounds which are oligomers are included in the mixtures. The compounds in the mixtures of the invention are distinguished from polymers according to the following relationship.

The qualitative relationship between the log viscosity (log $\eta$) to the log molecular weight (log MW) of a compound is linear. At a critical molecular weight (MWc) or critical viscosity ($\eta$c) the slope of a curve illustrating that relationship changes sharply, for example, from about 1 to about 3.4. Above MWc or $\eta$c the compound is polymeric. The melt viscosity of polymers will normally be so high as to prevent or retard the formation of the pits necessary for recording information on optical recording layers. Thus, polymeric compounds are excluded from the mixtures of the present invention. Below MWc or ηc, the compound is a monomer or an oligomer and is within the scope of this invention. MWc and ηc is not fixed, and varies with the structure of the particular compound. See *Fundamental Principles of Polymeric Materials for Practicing Engineers* by Stephen L. Rosen, Barnes and Noble, Inc., N.Y., N.Y., (1971), pages 176 and 177. In general, it is believed that compounds having a molecular weight up to about 5000 or up to about 10 recurring units are useful in the mixtures of this invention, although it is expected that compounds having a molecular weight greater than 5000 or more than 10 recurring units will in some circumstances be operable.

The novel method for making the mixtures of the invention comprises the step of reacting in stoichiometric amounts, at least one nonpolymeric compound having at least two reactive components with at least two other compounds having a single reactive component; provided that at least one of said compounds contains a multicyclic aromatic nucleus.

In one aspect of the method used to make the mixtures (a) at least one nonpolymeric compound having at least two reactive components selected from the group consisting of hydroxy, amine, aminoalcohols and aminophenols is reacted with (b) at least two other nonpolymeric compounds having a single reactive component selected from the group consisting of carboxylic acid, carboxylic acid derivatives and isocyanates.

In another aspect of the method (a) at least one nonpolymeric compound having at least two reactive components selected from the group consisting of carboxylic acid, carboxylic acid derivatives and isocyanates is reacted with (b) at least two other nonpolymeric compounds having a single reactive component selected from the group consisting of hydroxy, amine, aminoalcohols and aminophenols.

In the above methods, at least one of the compounds in (a) or (b) contains a multicyclic aromatic nucleus.

DETAILED DESCRIPTION OF THE INVENTION

The above methods involve well known reactions of an organic isocyanate, organic anhydride, or organic acid such as a carboxylic acid or sulfonic acid with an alcohol, phenol, or amine; or the reaction of a thioamide with an active halogen compound, such as an aromatic thioamide with a bromoketone or chloroacetyl substituted compound; or the reaction of a tetrazole with an acid halide to produce ester, amide, imide, urethane, nitrilomethyleneoxy, nitrilomethyleneimino, nitrilomethylenethio, 1,3,4-triazol-2,5-ylene and 1,3,4-oxadiazol-2,5-ylene linkages. Descriptions of these reactions are found in a variety of basic organic chemistry texts such as *Chemisty of Organic Compounds*, by C. R. Moller, W. B. Saunders Co., Philadelphia, PA., and in *Heat-Resistant Polymers* by V. V. Korshak, Keter Press, Jerusalem, Israel (1971). It is expected that known linking groups formed by other known chemical methods would also be suitable.

It is understood that the materials can be added during the preparative reaction in various sequences as is known in the art. For example, one of two similar reactants can be added first and allowed to react to completion before adding the second similar reactant. Such techniques facilitate control of the final compositions, especially of oligomers where molecular weight can be controlled by the order and rate of addition of reactants.

It is noted that as the number of selected reactants and the number of functionalities in each reactant increases, the number of different compounds in the mixture will increase. That number will also be affected by other variables familar to those skilled in the art such as the different reaction rates of the different reactants, reaction time, temperature, and feed rate. The approximate theoretical maximum number of different compounds can, however, be computed by well known mathematical principles and formulas relating to combinations and permutations (for example, *Modern Elementary Statistics*, Prentice Hall, Inc. Freund, page 75, 5th Ed. 1979).

While the presence of each individual compound in a complex mixture cannot be easily determined qualitatively or quantitatively, the presence of each nucleus ($Z^1$ and $Z^2$) and of each substuents ($R^1$, $R^2$ and $R^3$) can be determined qualitatively and quantitatively. Hence, in the following assigned structures for the mixtures of this invention, the mole percent of each component is assigned on the basis of the stoichiometric monomer feed ratios used in each preparation.

The assigned symbolic structures in Examples 1–5 and in Table I for the mixtures are designed to emphasize the random nature of the compounds in each mixture. Each nucleus ($Z^1$ and $Z^2$) on the left of the structure theoretically reacts with every substituent ($R^1$, $R^2$ and $R^3$) on the right side of the structure to form all compound permutations possible. Mixtures 9, 10 and 18 of Table I include compounds which are oligomers. In each mixture, reactants selected for $Z^1$ and some of the reactants selected for $R^2$ are bifunctional.

To obtain the amorphous solid mixture of the invention, the starting materials are chosen according to bulk and structural dissimilarity. Bulk refers to organic nuclei having relatively large size and/or volume. Bulk is necessary to insure the mixture is solid. Structural dissimilarity is necessary to insure that the mixture is amorphous.

Representative starting materials having a multicyclic aromatic nucleus and at least two functional (reactive) groups are selected from the following materials:

A. The phenylindan diols disclosed in *Research Disclosure*, Item No. 11833, February 1974, and U.S. Pat. Nos. 3,803,096, 3,859,364 and 3,886,124 and the phenylindan diamines of U.S. Pat. Nos. 3,897,253 and 3,915,939 having the structures:

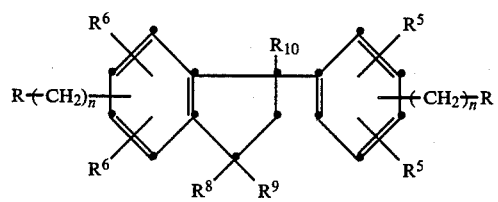

and

-continued

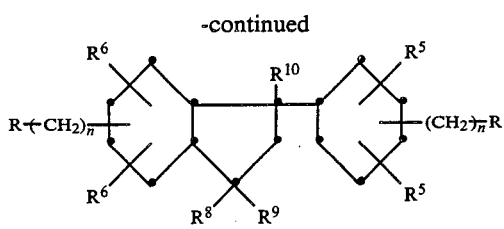

wherein
R is hydroxy or amino;
R$^8$ and R$^{10}$ are independently selected from the group consisting of hydrogen and alkyl radicals of from 1 to 6 carbon atoms;
R$^9$ is an alkyl radical of from 1 to 6 carbon atoms;
R$^5$ and R$^6$ are independently selected from the group consisting of hydrogen, aryl radicals, halogen atoms, nitro radicals, cyano radicals, amino radicals and alkoxy radicals;
n is 0 or 1.

B. The 1,1′-spirobiindan diols and diamines disclosed in U.S. Pat. No. 3,725,070; and the 1,1′-spirobiindan (dicarboxylic acids) of *Research Disclosure*, Item No. 9830, June 1972 (anonymous), having the structure:

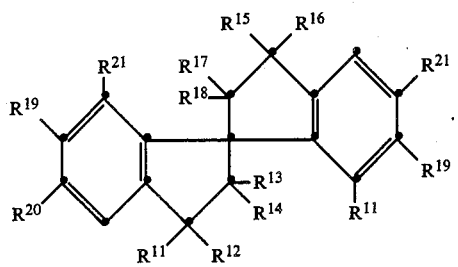

wherein
each R$^{21}$ independently is selected from the group consisting of hydrogen atoms, or alkyl radicals having 1 to 12 carbon atoms;
R$^{11}$, R$^{12}$, R$^{13}$, R$^{14}$, R$^{15}$, R$^{16}$, R$^{17}$, R$^{18}$ and R$^{20}$ are independently selected from the group consisting of hydrogen atoms and alkyl radicals of from 1 to 5 carbon atoms; and
R$^{19}$ is —OH, NH$_2$, or OCH$_2$COOH.

C. The 1,1′-spirobiindan-5,5′-diamines disclosed in *Research Disclosure*, Item No. 13117, March 1975, having the structure:

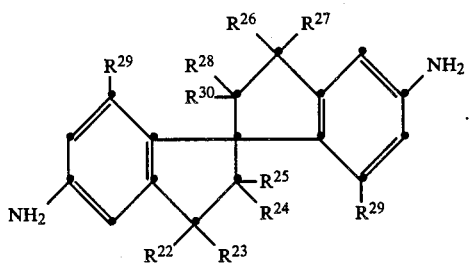

wherein
each R$^{29}$ is independently selected from hydrogen atoms and alkyl radicals of 1 to 12 carbon atoms; and
R$^{22}$, R$^{23}$, R$^{24}$, R$^{25}$, R$^{26}$, R$^{27}$, R$^{28}$ and R$^{30}$ are independently selected from the group consisting of hydrogen atoms and alkyl radicals of from 1 to 5 carbon atoms.

D. The 2,2′-spirobichromans disclosed in U.S. Pat. No. 3,859,097 having the structure:

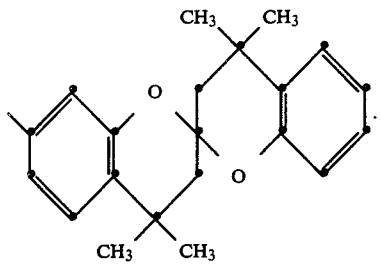

E. The 7,7-dimethyl-7H-dibenzo [c, h] xanthene diols disclosed in U.S. Pat. Nos. 3,859,254 and 3,902,904 having the structure:

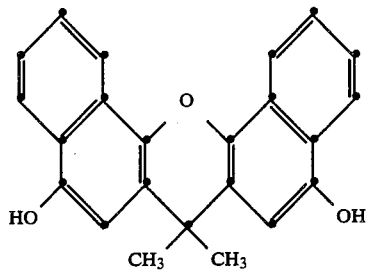

F. The 9,9-dimethylxanthene-3,6-bis-(oxyacetic acids) disclosed in *Research Disclosure*, Item No. 9830, June 1972, (anonymous) having the structure:

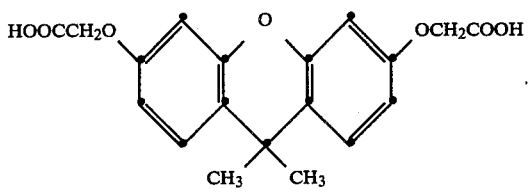

G. The xanthylium salts disclosed in U.S. Pat. No. 3,856,751, having the structure:

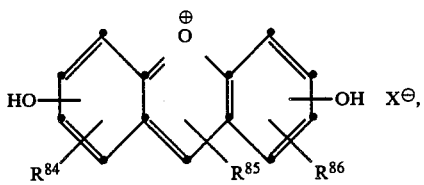

wherein
R$^{84}$, R$^{85}$ and R$^{86}$ are hydrogen, alkyl, aryl, halogen, alkoxy, or cyano; and
X is an acid anion.

H. The 4,4′-(3-phenyl-1-indanylidene)diphenols disclosed in *Research Disclosure*, Item No. 13101, March 1975, having the structure:

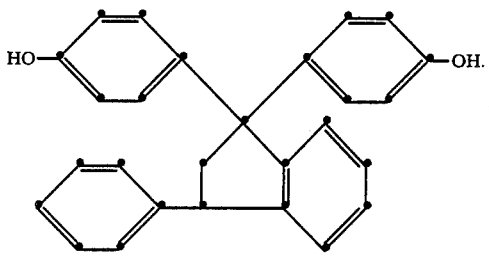

I. The 4,4'-(hexahydro-4,7-methanoindan-5-ylidene)-diphenols disclosed in *Research Disclosure*, Item No. 13568, July 1975, having the structure:

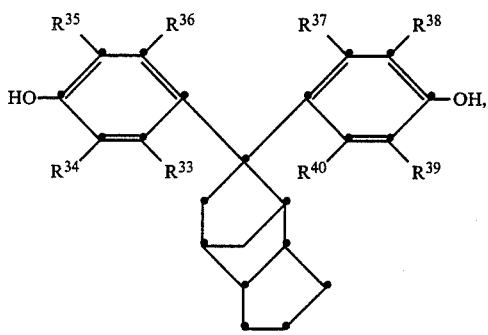

wherein
$R^{33}$, $R^{34}$, $R^{35}$, $R^{36}$, $R^{37}$, $R^{38}$, $R^{39}$ and $R^{40}$ are independently hydrogen, halogen, cyano, alkyl of 1 to 8 carbon atoms, or alkoxy of 1 to 8 carbon atoms.

J. The bisphenols disclosed in *Research Disclosure*, Item No. 13569, July 1975, having the structure:

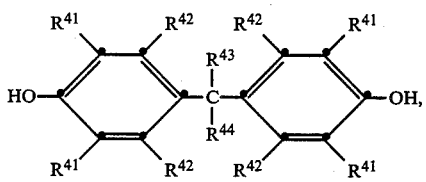

wherein
each $R^{41}$ is hydrogen, halogen, preferably chloro or bromo, alkyl of 1 to 8 carbon atoms, or alkoxy of 1 to 8 carbon atoms;
each $R^{42}$ is hydrogen, alkyl of 1 to 8 carbon atoms or alkoxy of 1 to 8 carbon atoms; and
$R^{43}$ and $R^{44}$ are alkyl of about 1 to 6 carbon atoms.

K. The sulfonyldibenzoic acids disclosed in *Research Disclosure*, Item No. 14016, December 1975, having the structure:

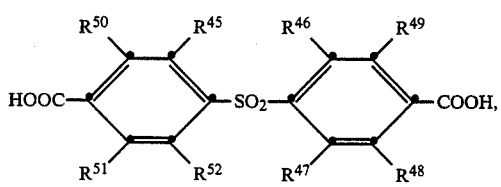

wherein
each of $R^{45}$ through $R^{52}$ is independently selected from hydrogen, halogen, preferably chloro or bromo, and alkyl of about 1 to 4 carbon atoms.

L. The polycyclic norbornanes of *Research Disclosure*, Item No. 9207, December 1971, (anonymous), having the structure:

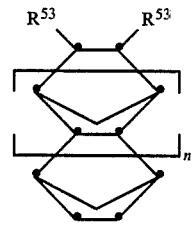

wherein
n is 0 to 3; and
$R^{53}$ is —COOH or —CH$_2$OH.

M. The 1,2,3,4-tetrahydronaphthalenes disclosed in *Research Disclosure*, Item No. 13570, July 1975, having the structure:

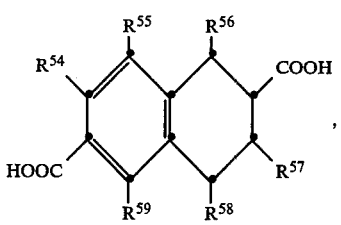

wherein
each of $R^{54}$ through $R^{59}$ is independently selected from hydrogen, halogen or lower alkyl of 1 to 4 carbon atoms.

Other useful polyfunctional compounds include commercially available bisphenols such as tetrabromophenolphthalein, tetrachlorophenolphthalein, tetrabromophenol blue, 4,4'-(1,2,3,4,7-7-hexachloro-2-norbornene-5-ylmethylene)bis(2,6-dibromophenol), 9,10-bis(hydroxymethyl)triptycene, 9,10-dicarboxytriptycene, Eosin B, tetrabromocresol blue, hematoxylin, 4',5'-diiodofluorescein, the polyhydroxy aromatic condensation product of pyrogallol and acetone, guercetin and derivatives thereof, 9,9-bis(4-amino-3-benzoylphenyl)-fluorene, 9,9-bis-(4-aminophenyl)-10-anthrone and derivatives thereof reported in Macromolecules 14, pp. 486–493 (1981), p-hydroxybenzoic acid and other multifunctional compounds which are susceptible to quantitative condensation to yield mixed esters, or mixed amides, or mixed imides, or mixed urethanes, or any other mixtures of organic materials that are readily soluble in organic solvent, noncrystallizable, and preferably have glass-transition temperatures well above room temperature, i.e., above 100° C., and more preferably above 150° C.

Useful starting materials having single reactive components include:

A. Substituted benzene functionalized compounds having the structure:

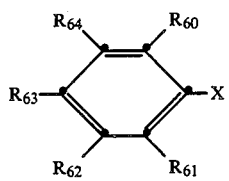

wherein
R$_{60}$ through R$_{64}$ are independently selected from the group consisting of hydrogen, aryl radicals, halogen atoms, nitro radical, cyano radicals, amino radicals and alkoxy radicals, or any pair of R$^1$-R$^5$ occupying adjacent carbon atoms can be taken together to represent a fused ring or fused ring system.

X is selected from the group consisting of primary or secondary amino radicals, hydroxy radicals, acid radicals, isocyanate radicals.

B. Substituted phthalic anhydride compounds having the structure:

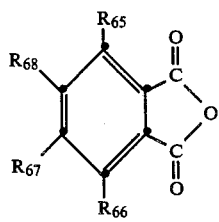

wherein
R$_{65}$ through R$_{68}$ are independently selected from the group consisting of hydrogen, aryl radicals, halogen atoms, nitro radicals, cyano radicals, amino radicals, and alkoxy radicals.

C. Aliphatic acids, alcohols, isocyanates, amines, and derivatives thereof.

D. Compounds having unsaturated polymerizable or crosslinkable groups such as acrylic acid, methacrylic acid and derivatives thereof, allyl alcohol, etc.

The following examples illustrate the preparation of the mixtures of the invention. Glass transition temperatures were determined by differential scanning calorimetry analysis at a heating rate of 10°/min. or 20°/min. as specified.

EXAMPLE 1

Preparation of a mixture (1) having the structure:

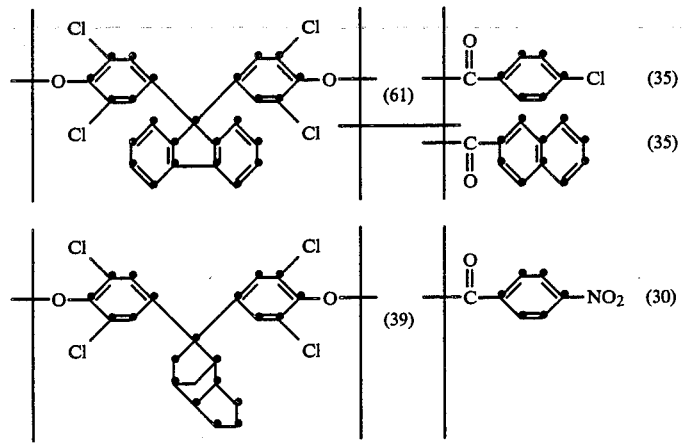

The compounds 9,9-Bis(4-hydroxy-3,5-dichlorophenyl)fluorene (0.081 mole), 4,4'-hexahydro-4,7-methanoindan-5-ylidene bis(2,6-dichlorophenol) (0.0518 mole), 1-naphthoyl chloride (0.0930 mole), p-chlorobenzoyl chloride (0.0930 mole) and p-nitrobenzoyl chloride (0.0797 mole) were all dissolved in approximately 1 liter of 1,2-dichloroethane in a three-neck, round-bottomed flask. A condenser fitted with a drying tube and a positive-pressure nitrogen system was used to keep moisture out of the reactor vessel.

Triethylamine (0.30 mole) dissolved in 100 ml of 1,2-dichloroethane was added dropwise to the stirred solution in the reaction flask. After complete addition of the triethylamine, the reaction was allowed to continue for three additional hours at which time a precipitated salt is filtered off. The reaction mixture was subjected to the following extraction sequence:
a. two dilute sodium hydroxide solution washes (2% cold)
b. two dilute hydrochloric acid solution washes (4%)
c. two distilled water washes The dichloroethane solution was then dried over magnesium sulfate and removed by evaporation at 90° C. under vacuum. One hundred ml of tetrahydrofuran (THF) was added to the dried amorphous glass mixture. The solution obtained was stirred into 4 liters of distilled water in a Waring Blender to precipitate the product. The product was collected by filtration as very fine particles and dried. The Tg was 101° C. (20°/min., differential scanning calorimetry).

EXAMPLE 2

Preparation of a mixture (2) having the structure:

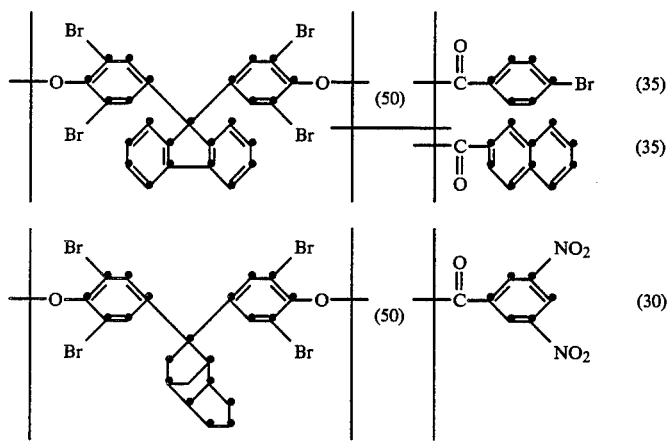

This mixture was prepared using the procedure of Example 1 from 0.081 mole of 4,4'-hexahydro-4,7-methanoindan-5-ylidene bis(2,6-dibromophenol), 0.081 mole of 9,9-bis(4-hydroxy-3,5-dibromophenyl)fluorene, 0.1134 mole of p-bromobenzoyl chloride, 0.0972 mole of 3,5-dinitrobenzoyl chloride, 0.1134 mole of 1-naphthoyl chloride and 35 g of triethylamine. The mixture Tg was 128° C. (20°/min., differential scanning calorimetry).

EXAMPLE 3

Preparation of a mixture (3) having the structure:

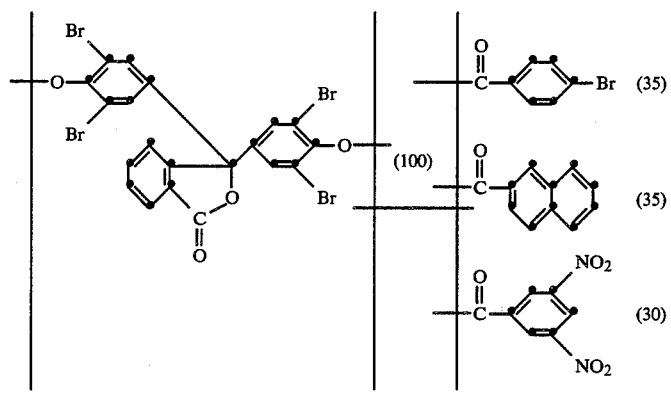

This mixture was prepared using the same procedure as in Example 1 from 0.1262 mole of 3',3'',5',5''-tetrabromophenolphthalein, 0.0883 mole of p-bromobenzoyl chloride, 0.0757 mole of 3,5-dinitrobenzoyl chloride, 0.0883 mole of 1-naphthoyl chloride and 27 g of triethylamine. The mixture Tg was 138° C. (20°/min., different scanning calorimetry).

EXAMPLE 4

Preparation of a mixture (4) having the structure:

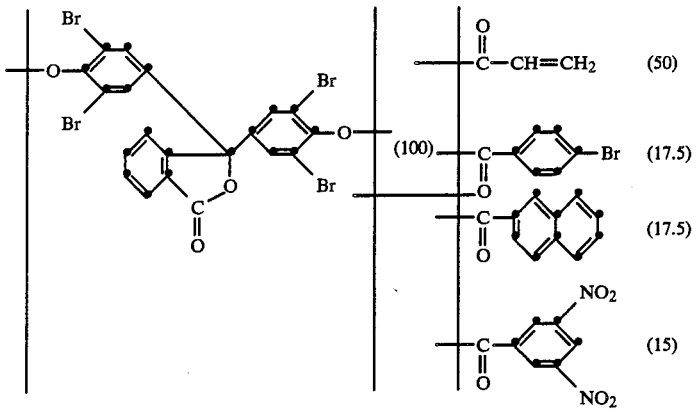

This mixture was prepared as in the procedure of Example 1 from 80 g (0.126 mole) of 3',3'',5',5''-tetrabromophenolphthalein, 11.43 g (0.1262) of acryloyl chloride, 9.70 g (0.0442 mole) of p-bromobenzoyl chloride, 8.73 g (0.0379 mole) of 3,5-dinitrobenzoyl chloride, 8.42 g (0.0442 mole) of 1-naphthoyl chloride and 27 g of triethylamine. However, before removal of the solvent ~0.5% of hydroquinone was added as a thermal stabilizer. The mixture Tg was 115° C. (20°/min., differential scanning calorimetry).

EXAMPLE 5

Preparation of a mixture (5) having the structure:

bromophthalic anhydride (0.0115 mole) tetrachlorophthalic anhydride (0.0186 mole) and naphthalic anhydride (0.0086 mole) in powder form (well mixed before addition) were added in small portions to the stirred amine solution. After complete addition the solution was refluxed for 2½ hours.

While the mixture was still hot, 6 ml of pyridine, and 6 ml of acetic anhydride was added and stirring continued for another hour. The mixture was then poured into two liters of distilled water and the product collected by filtration. The light yellow solid was taken into dichloromethane, washed successively with dilute sodium hydroxide, hydrochloric acid and water. The dichloromethane solution was concentrated to half its original volume and precipitated into heptane, collected and dried. The mixture Tg was 190° C. (20°/min).

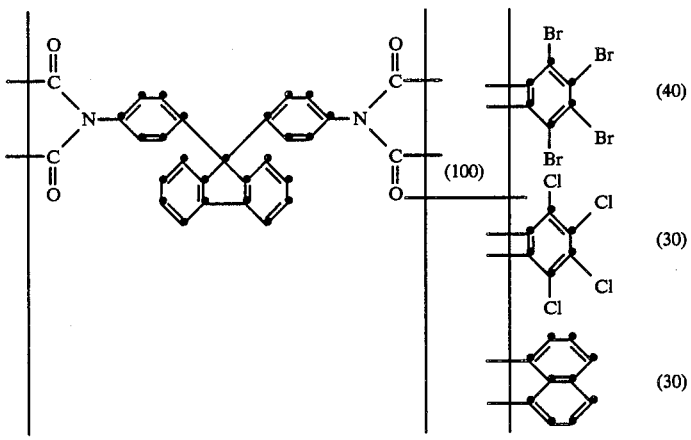

9,9-Bis(4-aminophenyl)fluorene (0.0144 mole), was dissolved in 20 ml of N,N-dimethylformamide. Tetra- Table I presents additional mixtures which were prepared.

TABLE I
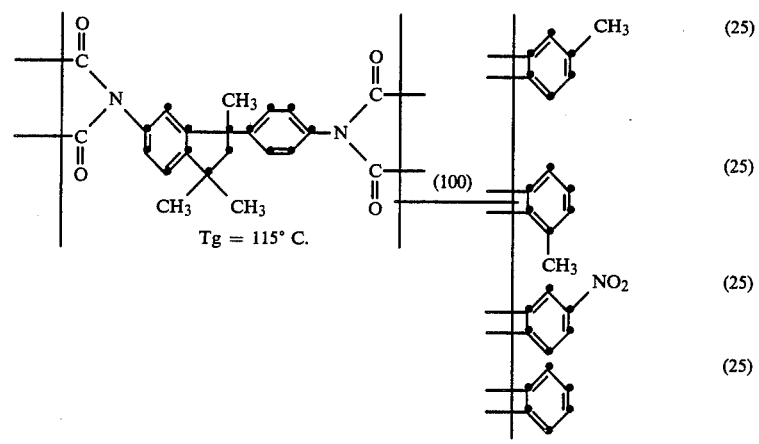
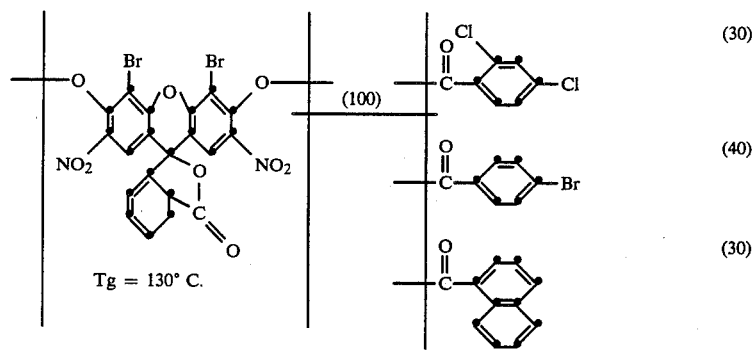
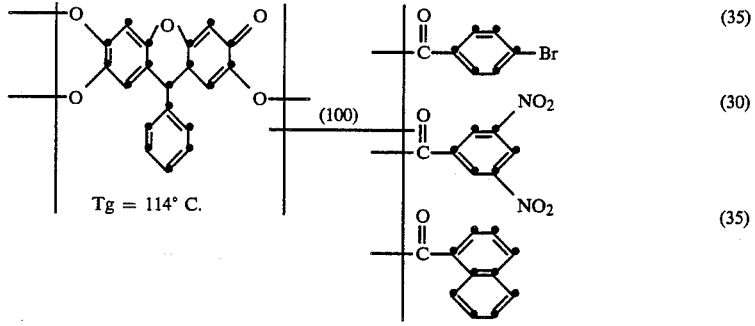
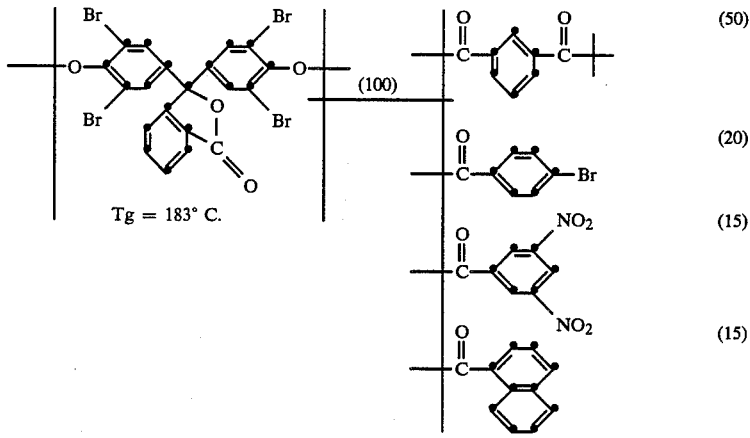

TABLE I-continued
10. 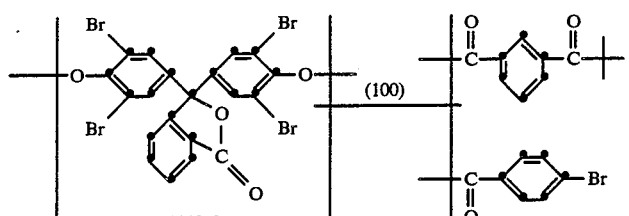 (100) 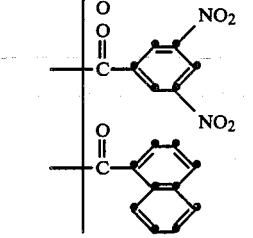 (75) (8.33) (8.33) (8.33)
Tg = 220° C.
11. 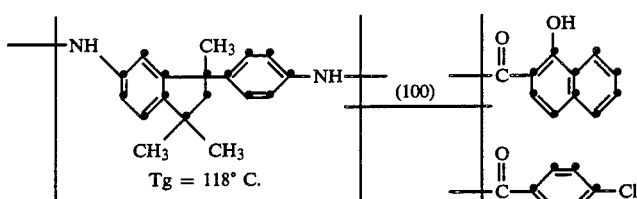 (100) 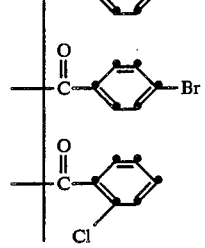 (50) (16.67) (16.67) (16.67)
Tg = 118° C.
12. 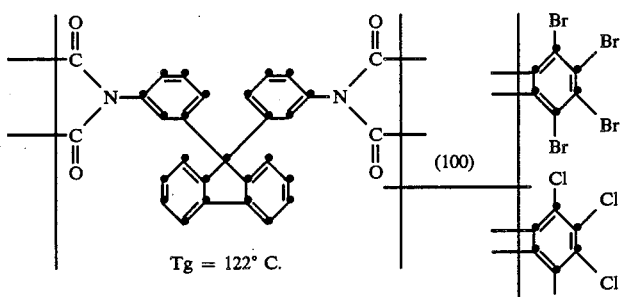 (100) 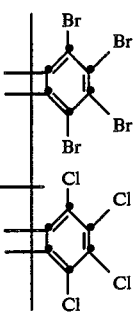 (40) (20) 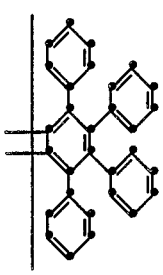 (40)
Tg = 122° C.

TABLE I-continued
13. 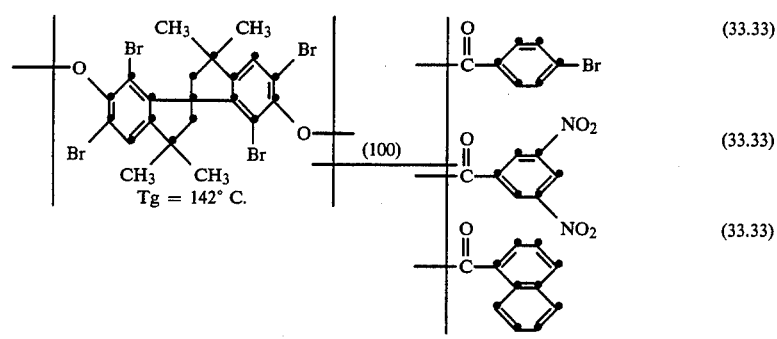 (33.33) (33.33) (33.33) (100)
14. 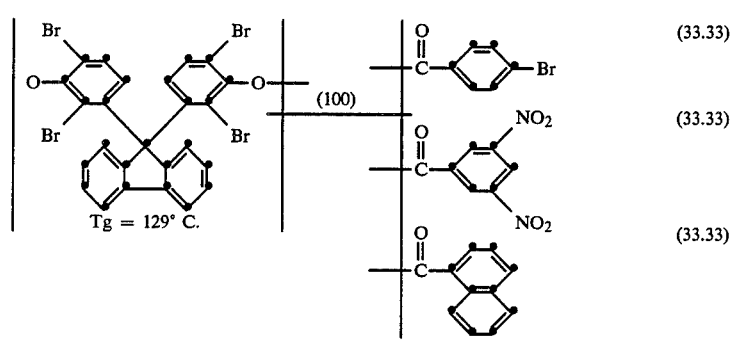 (33.33) (33.33) (33.33) (100)
15. 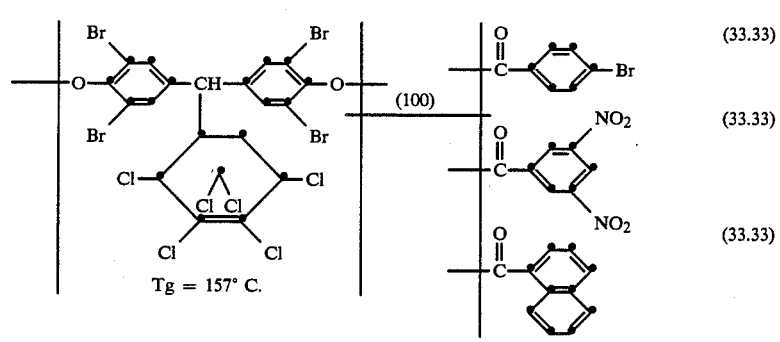 (33.33) (33.33) (33.33) (100)
16. 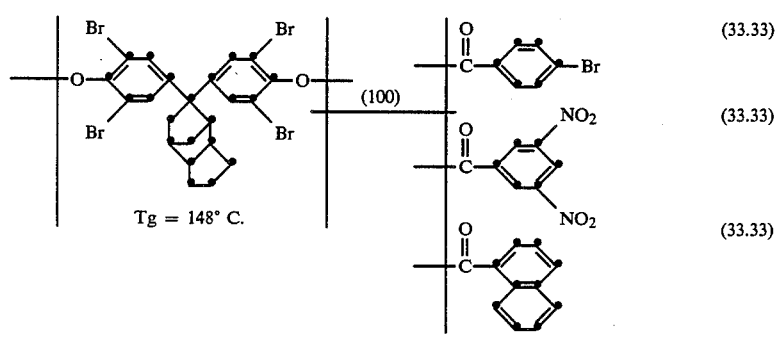 (33.33) (33.33) (33.33) (100)
17. 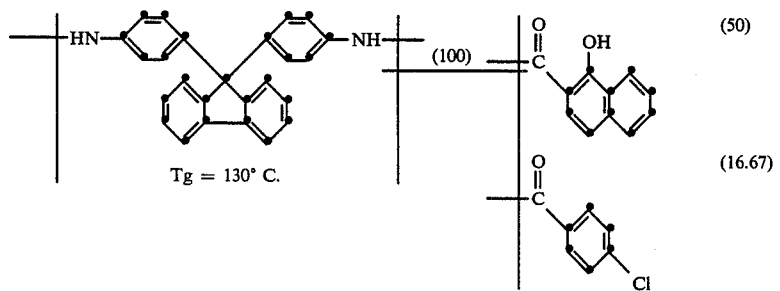 (50) (16.67) (100)

TABLE I-continued

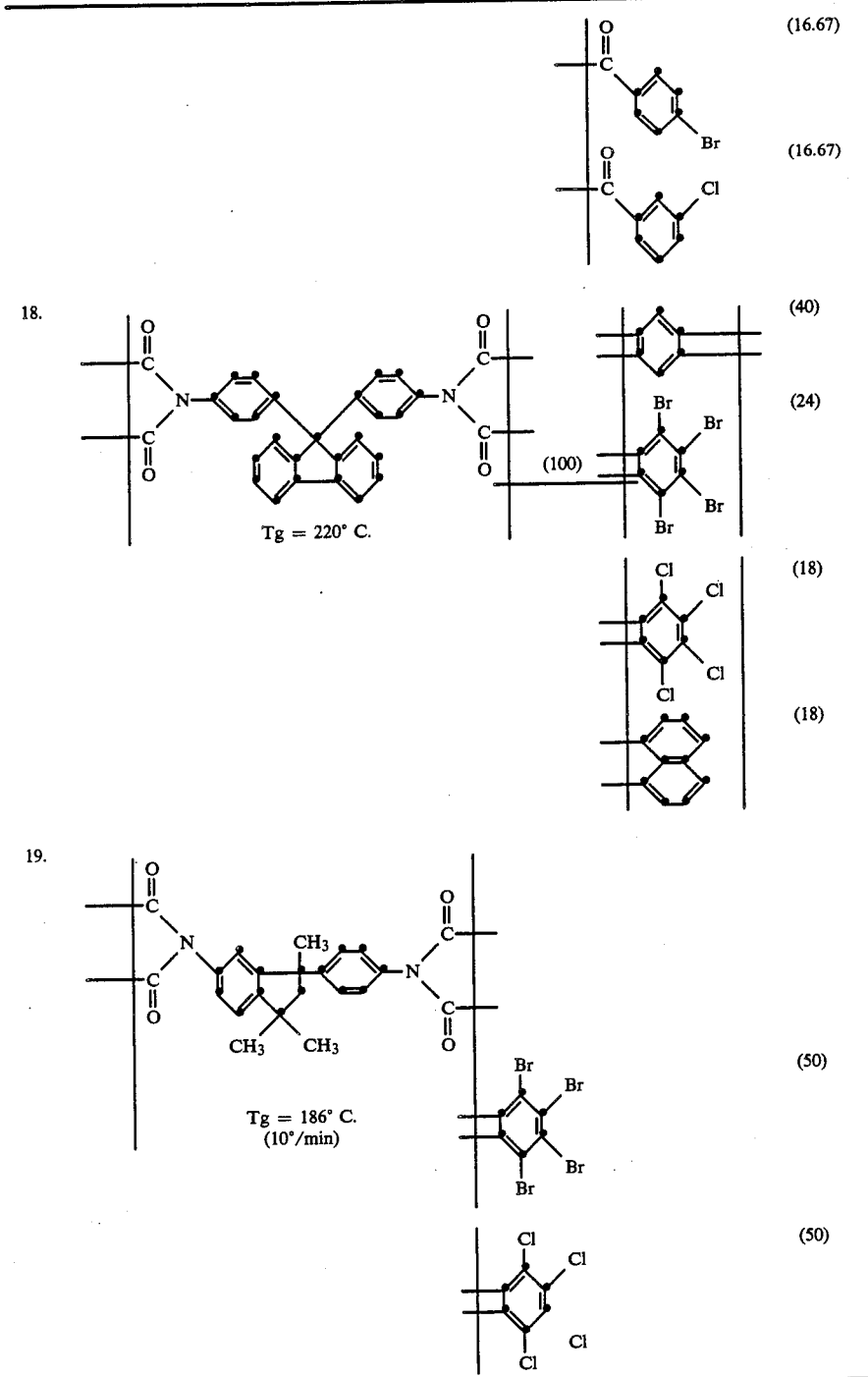

The optical recording and recorded information elements of the invention comprise a support having thereon a recording layer of a dye and as binder, a mixture of the invention. Depending upon the desired mode of reading the element, the support is either reflective or transparent. In the case of a reflective support, preferably both sides of the support are reflective and a recording layer is provided on both sides. The support is any of a wide variety of materials including for example, glass plate, glass plate coated with a 500 Å-thick reflective layer of aluminum, a resin film or plate such as poly(ethylene terephthalate), poly(methyl methacrylate), poly(vinyl chloride), polystyrene or cellulose acetate, paper, clay, wood or metal. Important characteristics of the support are that it have a relatively high melting point (to avoid deformation during recording), have a very smooth surface (to minimize noise), and be capable of being coated with a layer of amorphous material, with good adhesion and no significant chemical reactivity between the layer and the useful support.

Useful dyes are chosen for their compatibility with the binder of choice and for high absorptivity at the wavelength of the recording laser beam. Innumerable dyes are available and well-known. When the recording beam is one produced by an argon-ion laser (wavelength=488 nm), useful dyes include but are not limited to: Iosol Red (CI solvent red 68) ($e_{488}$/MW=40); Eastone Red R (available from Eastman Kodak Company) having the structural formula:

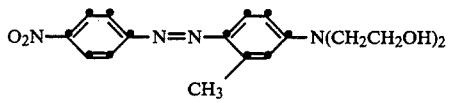

N,N-bis(2-hydroxyethyl)-3-methyl-4-(4-nitrophenylazo)aniline;
Eastone Red B (available from Eastman Kodak Company) having the structural formula:

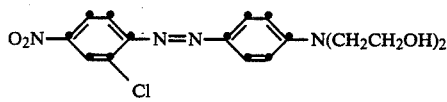

N,N-bis(2-hydroxyethyl)-4-(3-chloro-4-nitrophenylazo)aniline;
Sudan IV, having the structural formula:

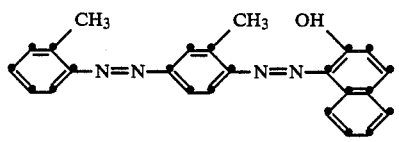

1-[4-(2-tolylazo)-2-tolylazo]-2-naphthol;
1-(2-pyridylazo)-2-naphthol having the structural formula:

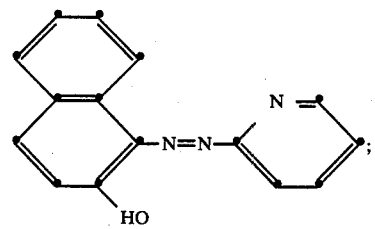

a dye referred to as SK1 having the structural formula:

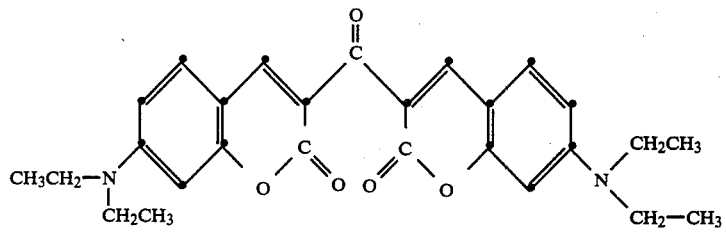

p 3,3'-carbonylbis(7-diethylaminocoumarin); and
a dye referred to as SK2 having the structural formula:

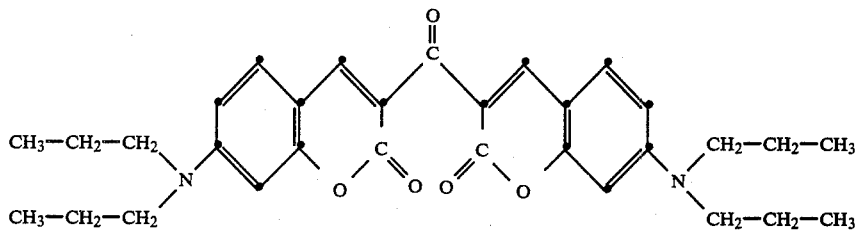

3,3'-carbonylbis(7-dipropylaminocoumarin).

The preparation of compounds such as SK1 and SK2 and other useful coumarins is described in *Research Disclosure*, Item 16167, September, 1977. *Research Disclosure* is published by Industrial Opportunities Ltd., Homewell, Havant, Hampshire, P09 1EF, UK.

Another group of useful dyes have the structure:

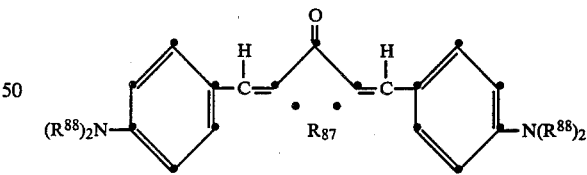

wherein $R_{87}$ is $(CH_2)_n$ or $CH_2-\underset{\underset{CH_3}{|}}{N}-CH_2$;

n is an integer from 0–5 and each $R^{88}$ is independently selected from the group consisting of straight- and branched-chain alkyl groups of about 1–6 carbon atoms.

These dyes have a high extinction coefficient at 488 nm. Included within the above structure are dyes such as 2,3-bis(4-dimethylaminobenzylidene)cyclopropanone; 2,5-bis[4-(N-t-butyl-N-methylamino)benzylidene]cyclopentanone; 2,5-bis(4-diethylaminobenzylidene)cyclopentanone; 2,6-bis(4-diethylaminobenzylidene)cyclohexanone; 1,3-bis(4-diethylaminobenzylidene)acetone and 3,5-bis(4-diethylaminobenzylidene)-1-methyl-4-piperidone.

Indolizine and indolizinium dyes of the type disclosed in U.S. patent application Ser. No. 391,769, filed June 24, 1982, U.S. Pat. No. 4,446,223 by Fletcher et al are useful in optical recording elements. Such dyes conform to the structures:

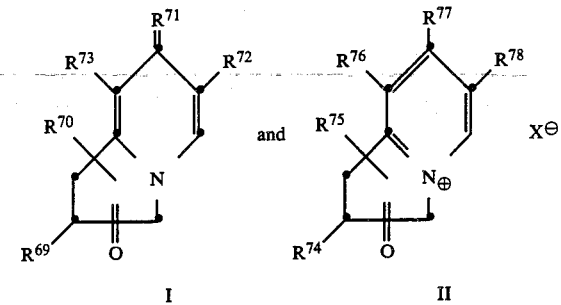

wherein
X⊖ is an anion, preferably an acid anion;
$R^{69}$ and $R^{70}$ are individually selected from straight and branched alkyl containing 1 to 18, preferably 1 to 10 carbon atoms, such as methyl, ethyl, propyl and decyl; aryl containing 6 to 20 carbon atoms, such as phenyl, tolyl, xylyl, methoxyphenyl, 4-t-butylphenyl, anisyl, naphthyl and methoxynaphthyl; and polystyryl having appended groups selected from the group consisting of indolizine and indolizinium groups and combinations thereof;
$R^{71}$ is a divalent group which with the indolizinone nucleus completes an organic chromophore;
$R^{72}$ is hydrogen or a substituent that does not adversely affect desired dye properties, such as alkyl containing 1 to 18 carbon atoms, such as methyl, ethyl and dodecyl; cyano; acyl containing 2 to 18 carbon atoms, such as acetyl, propionyl, 2-ethylhexanoyl and stearoyl; carboalkoxy containing 1 to 18 carbon atoms, such as carbomethoxy, carboethoxy and carbobutoxy; aminocarbonyl, such as unsubstituted aminocarbonyl, methylaminocarbonyl, dimethylaminocarbonyl and ethylaminocarbonyl; acyloxy containing 2 to 18 carbon atoms, such as acetoxy, propionoxy, butyroxy and lauroyloxy; bromine and chlorine; and
$R^{73}$ is hydrogen or a substitutent that does nmot adversely affect desired dye properties, such as hydrogen, chlorine, bromine or alkyl containing 1 to 18 carbon atoms, such as methyl, ethyl, propyl, and dodecyl;
$R^{74}$ and $R^{75}$ are individually alkyl containing 1 to 18, preferably 1 to 10 carbon atoms, such as methyl, ethyl, propyl and decyl;
aryl containing 6 to 20 carbon atoms, such as phenyl, tolyl, xylyl, methoxyphenyl, 4-t-butylphenyl, anisyl, naphthyl and methoxynaphthyl; and
polystyryl having appended groups selected from the group consisting of indolizine and indolizinium groups and combinations thereof;
$R^{77}$ is a monovalent group which with the oxoindolizinium nucleus completes an organic chromophore;
$R^{78}$ is hydrogen or a substituent that does not adversely affect desired dye properties, such as alkyl containing 1 to 18 carbon atoms, such as methyl, ethyl, and dodecyl; cyano; acyl containing 2 to 18 carbon atoms, such as acetyl, propionyl, 2-ethylhexanoyl and stearoyl; carboalkoxy containing 1 to 18 carbon atoms, such as carbomethoxy, carboethoxy and carbobutoxy; aminocarbonyl, such as unsubstituted aminocarbonyl, methylcarbonyl, dimethylaminocarbonyl, and ethylaminocarbonyl; acyloxy containing 2 to 18 carbon atoms, such as acetoxy, propionoxy, butyroxy and lauroyloxy; bromine and chlorine; and
$R^{76}$ is hydrogen or a substituent that does not adversely affect desired dye properties, such as hydrogen, chlorine, bromine or alkyl containing 1 to 18 carbon atoms, such as methyl, ethyl, propyl and dodecyl.

Useful $R^{71}$ and $R^{77}$ groups are, for example:
(a) substituted or unsubstituted heterocyclyl or heterocyclylidene groups optionally appended through methine and polymethine groups, such as (i) indolizine and indolizinium groups illustrated by structures (I) and (II) appended directly as the respective $R^3$ and $R^8$ groups or appended through a substituted or unsubstituted methine or polymethine chain, such as containing 1 to 6 methine groups, (ii) pyridylidene, (iii) pyranyl, (iv) pyranylidene, (v) thiopyranyl, (vi) thiopyranylidene, and (vii) julolidyl; including the onium salts of such heterocyclyl and heterocyclylidene groups, such as the immonium, oxonium and sulfonium salts; and the acid addition salt derivatives of such heterocyclyl and heterocyclylidene groups;
(b) substituted and unsubstituted aminoarylmethine and hydroxyarylmethine, including their tautomers, such as represented by the formula: (L)(A)(D) wherein
L is a methine or polymethine group, containing 1 to 6 methine groups such as trimethine;
A is a substituted or unsubstituted aromatic group, such as arylene containing 6 to 20 carbon atoms, for example, phenylene, phenylidyne, naphthylene, and naphthylidyne; and
D is $-OR^{79}$, $-NR^{80}R^{81}$, $=O$, or $=NR^{82}$
wherein $R^{79}$ is a monovalent cation, preferably hydrogen, $R^{80}$ and $R^{81}$ are independently selected from hydrogen, substituted or unsubstituted alkyl, such as alkyl containing 1 to 20 carbon atoms, alkenyl, such as alkenyl containing 2 to 20 carbon atoms, and aryl, such as aryl containing 6 to 20 carbon atoms, including phenyl and tolyl; or, $NR^{80}R^{81}$ taken together with (A) form a polycyclic heterocyclic group, such as a 9-julolidyl group;
$R^{82}$ is alkyl, such as alkyl containing 1 to 20 carbon atoms or aryl such as aryl containing 6 to 20 carbon atoms;
(c) a methylene group substituted with at least one, preferably two electronegative groups, such as acyl, cyano, aryl, alkoxycarbonyl, and aminocarbonyl groups; and
(d) a formyl group.

X⊖ is an anion, for example, methanesulfonate, trifluoromethanesulfonate, para-toluenesulfonate, bromide, chloride, iodide, and sulfinate.

Preferred indolizine and indolizinium dyes include:

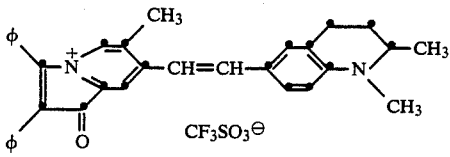

7-[2-(1,2-dimethyl-1,2,3,4-tetrahydro-6-quinolinyl)-1-ethenyl]-2,3-diphenyl-6-methyl-1-oxoindolizinium trifluoromethanesulfonate;

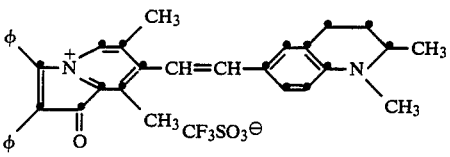

7-[2-(1,2-dimethyl-1,2,3,4-tetrahydro-6-quinolinyl)-1-ethenyl]-2,3-diphenyl-8-methyl-1-oxoindolizinium trifluoromethanesulfonate;

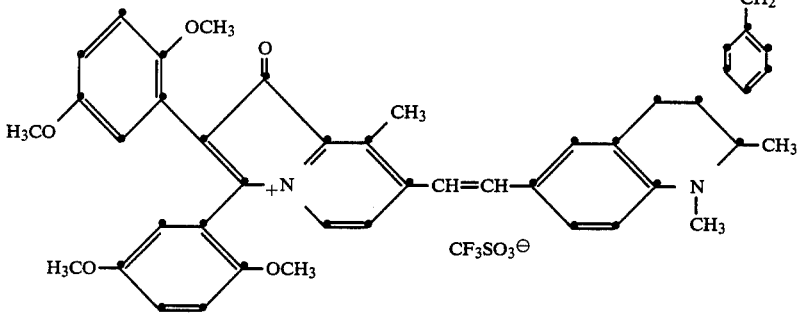

7-[2-(1,2-dimethyl-1,2,3,4-tetrahydro-6-quinolinyl)-1-ethenyl]-2,3-di(2,5-dimethoxyphenyl)-8-methyl-1-oxo(1H)-indolizinium trifluoromethane sulfonate. Mixtures of these dyes are also useful.

A preferred group of dyes which are especially compatible with the binder-mixtures of the present invention are defined as metal complexes of bis-[cis-1,2-bis-(alkyl, hydrogen, aryl or heterocyclic)ethylene-1,2-dithiene. They are also defined more simply as metal dithiene complexes. These dyes are infrared absorbers and are represented by the following formula:

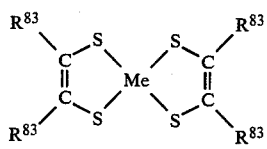

wherein:
Me is a metal of the first, second or third transition metal series. This includes elements of Group VIII of the periodic table such as nickel, palladium, or platinum.

Each $R^{83}$ is independently hydrogen, alkyl, or an aromatic or heterocyclic ring, or a substituted derivative thereof such as alkoxyalkyl, alkyl and/or alkoxy-substituted aromatic and heterocyclic rings, or 2 R groups substututed on adjacent carbon atoms can be taken together to form a fused ring or ring system, also optionally substituted with groups as mentioned above.

Examples of useful alkyl radicals contemplated for $R^{83}$ include, lower alkyl or alkoxy radicals containing 1–6 carbon atoms, such as methyl, ethyl, propyl, isopropyl, butyl, methoxy, ethoxy and propoxy. Examples of useful aromatic rings, including substituted derivatives thereof, include phenyl, naphthyl, tolyl, methylnaphthyl, alkoxyphenyl and alkoxynaphthyl, such as methoxyphenyl and dodecyloxyphenyl, halo-substituted phenyl, particularly fluoro-substituted phenyl, alkylthio-substituted phenyl, amino, including dialkylamino-substituted phenyl, haloalkyl-substituted, such as trifluoromethyl-substituted phenyl and naphthyl radicals.

Preferred metal dithienes include:

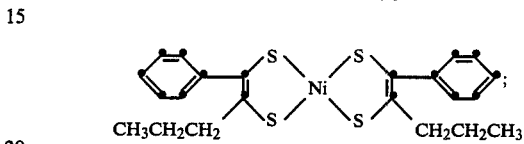

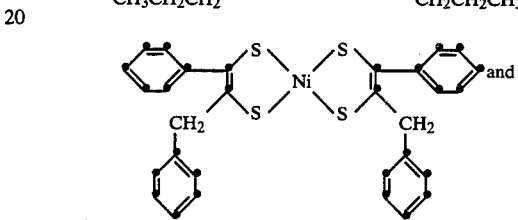

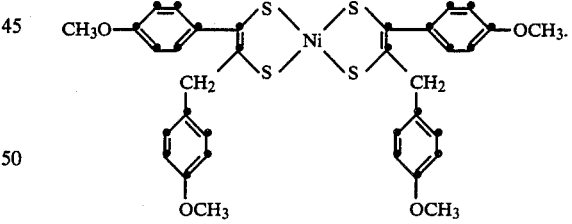

Mixtures of said dyes are also useful.

In certain applications the support is coated with a smoothing layer prior to the coating of the reflective layer, if any, and the described recording layer. The composition which is used to form the smoothing layer is preferably a low-viscosity, polymerizable fluid which is coated on the surface of the support. Following coating, polymerization of the fluid produces a microsmooth surface on the support. The procedure can be repeated to further improve smoothness. The support is made reflective, for example, by vacuum metalization of the smooth surface. In preferred embodiments, the polymerizable fluid comprises photopolymerizable monomers. Preferably, the monomers are low-viscosity fluids in the absence of solvents. Useful polymerizable fluid compositions are described in U.S. Pat. Nos. 4,092,173 and 4,171,979.

The support is optionally coated with other layers, as is known in the art. For example, preferably prior to coating the recording layer, the surface of the support is coated with a spacer layer which is substantially transparent to both write and read wavelengths. Such a spacer layer preferably has a refractive index which creates an interface of low dielectric contrast with the recording layer. The use of such a spacer layer is described by A. E. Bell and F. W. Spong, IEEE *Journal of Quantum Electronics*, July, 1978, page 487.

The recording layer comprising a dye and a binder-mixture of the invention is coated by any of a wide variety of methods. Most conveniently, the dye and binder are coated from a common solvent or, alternatively, from a mixture of miscible solvents. The dye-binder composition is coated by spray coating, air knife coating, whirl coating or by any other suitable method. The thickness of the recording layer according to the present invention is not critical; however, best results are obtained when the thickness of the layer is between about 0.1 and about 10 microns.

A thermal and mechanical barrier layer is optionally coated over the recording layer of the optical recording element. The purpose of this thermal and mechanical barrier layer is to protect the recording layer from defects such as scratches, dirt and fingerprints. Another function of the thermal and mechanical barrier layer is to prevent the material which is vaporized from the recording layer from depositing on the optical system and other components of the recording apparatus. Still another function of the thermal and mechanical barrier layer is to retain the heat which is generated in the recording layer by the writing beam.

Many materials have been proposed for the thermal and mechanical barrier layer which is coated over the recording layer of an ablative-type optical recording element. Bartolini et al in "Materials for Optical Recording" in a final report for Contract MDA904-76-C-0429 for the National Security Agency, August, 1977, reported experiments with a wide variety of overcoat materials. Especially useful thermal and mechanical barrier layers comprising water-soluble polymers having a glass transition temperature when dry of at least 100° C. are disclosed in Hollister et al U.S. Pat. No. 4,340,655.

Optimization of the recording elements of the present invention is described in U.S. Pat. No. 4,360,908 of Howe and Wrobel. Preferred disc configurations are described in a commonly assigned application entitled "Improved Optical Disc Method, Media And Apparatus For Writing And/Or Reading Information", filed June 18, 1980, U.S. Ser. No. 160,769, U.S. Pat. No. 4,447,899 in the names of Geyer and Howe.

The following examples are presented to illustrate the utility of the mixtures of the invention as binders in optical recording elements.

EXAMPLES 6-17

These examples illustrate the compatibility of the amorphous-binder mixture of the invention with various metal dithiene IR absorbing dyes.

In a compatible binder-mixture/dye composition, the composition has a single glass transition temperature. Compatibility was evaluated using thermal analysis techniques.

Twelve different samples were prepared of compositions comprising the binder-mixture of the present invention and a dye or a combination of two dyes selected from the following dyes:

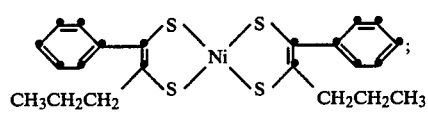
I.

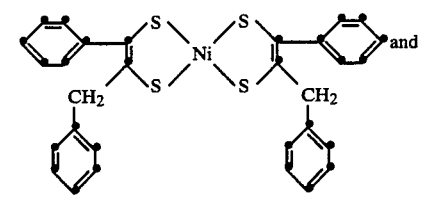
II.

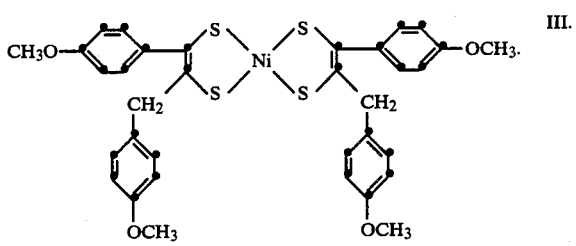
III.

The samples were prepared by mixing the dye and the binder into dichloromethane which was subsequently removed before the thermal analysis.

The nickel dithiene IR dyes described above were found compatible with the mixtures of the invention, even with concentrations as high as 70% dye, as evidenced by the results presented in Table II showing that the binder-mixture/dye composition has a single glass transition temperature.

TABLE II

| | | Compatibility Evaluation | | | | |
|---|---|---|---|---|---|---|
| Examples | Binder-Mixture | Binder-Mixture Tg, °C. | Dye | Dye Tg, °C. | Wt % Dye | Dye/Binder-Mixture Tg, °C. |
| 6 | 1 | 101 | I | 8 | 50 | 48 |
| 7 | 1 | 101 | II | 27 | 50 | 55 |
| 8 | 1 | 101 | III | 53 | 56.8 | 80 |
| 9 | 1 | 101 | I/II* | 8/27 | 60 | 45 |
| 10 | 1 | 101 | I/III* | 8/53 | 60 | 54 |
| 11 | 2 | 128 | I | 8 | 50 | 50 |
| 12 | 2 | 128 | I/II* | 8/27 | 60 | 49 |
| 13 | 3 | 138 | I | 8 | 50 | 55 |
| 14 | 3 | 138 | II | 27 | 50 | 74 |
| 15 | 3 | 138 | I/II* | 8/27 | 60 | 54 |
| 16 | 3 | 138 | I/III* | 8/53 | 60 | 59 |

TABLE II-continued

|  | | Compatibility Evaluation | | | | |
| --- | --- | --- | --- | --- | --- | --- |
| Examples | Binder-Mixture | Binder-Mixture Tg, °C. | Dye | Dye Tg, °C. | Wt % Dye | Dye/Binder-Mixture Tg, °C. |
| 17 | 5 | 152 | I | 8 | 50 | 80 |

*A combination of the two indicated dyes at a 1:1 weight ratio were used in these examples. The two numbers are the Tg's for the respective dyes.

EXAMPLE 18

This example demonstrates the absorption stability of compositions comprising a dye and a binder-mixture 1 of Example 1 of the present invention compared to compositions comprising the same dye and cellulose nitrate as the binder.

Solutions of a binder and a nickel dithiene dye (1:1) were prepared and spin coated over 2×2 glass slides. The glass slides were incubated at specific thermal and relative humidity (RH) conditions and analyzed for absorption loss spectrophotometrically before and after incubation. The results are shown in Table III below.

TABLE III

| Binder | Dye | Absorption Loss (%) | | |
| --- | --- | --- | --- | --- |
|  |  | 100° F./50% RH 2 week % loss | 100° F./80% RH 2 week % loss | 120° F./50% RH 2 week % loss |
| binder-mixture 1, example 1 | I | 0.2 | 0.85 | 0.83 |
| binder-mixture 1, example 1 | II | 1.5 | 1.5 | 1.6 |
| binder-mixture 1, example 1 | III | 0.87 | 2.4 | +1.6* |
| Control Cellulose Nitrate | I | 2.8 | not tested | 20.4 |

*represents an increase in absorption

EXAMPLE 19

This example demonstrates the utility of the binder-mixtures of the present invention in optical recording elements.

A 300 mm-diameter circular glass substrate was whirl-coated with a surface-smoothing composition by flooding the glass substrate with the smoothing composition at low rpm (about 80–100 rpm) and then leveling the coating by advancing the speed to about 500 rpm. The surface-smoothing composition comprised:

| | |
| --- | --- |
| pentaerythritol tetraacrylate | 20 g |
| a low-viscosity urethane-acrylate monomer (UV-curable Topcoat 874-C-2002 TM, Fuller O'Brien Corp.) | 20 g |
| 2-ethoxyethanol | 60 g |
| a coumarin sensitizer composition | 3 g |
| surfactant | 3 drops |

The coated and dried surface-smoothing composition was cured by irradiating with a 3000-watt pulsed xenon arc lamp at 18 inches for 4 minutes. A layer of aluminum about 500 Å thick was vapor deposited on top of the surface-smoothing layer.

A dye/binder-mixture composition consisting of a 50:50 mixture of nickel dithiene dye I and binder-mixture 1 of Example 1 was spincoated over the aluminized-surface-smoothed 12-inch glass disk. This prepared element was recorded upon with a diode laser emitting at about 800 nm, pulsed at 10 MHz and a 50% duty cycle in a 30 KHz band width. The element was read back by monitoring the feedback from a HENe (633 nm) laser. The signal-to-noise ratio ranged from 40 to 53 at 633 nm at laser beam incident peak power varying from 8 to 12 milliwatts.

The invention has been described in detail with particular reference to preferred embodiments thereof, but it will be understood that variations and modifications can be effected within the spirit and scope of the invention.

What is claimed is:

1. A composition comprising a mixture of non-polymeric compounds exhibiting a single thermal transition free of phase separation characterized in that said mixture (a) is amorphous (b) is solid at about 20° C. and (c) comprises at least two different compounds each having at least two linking components joining one multivalent organic nucleus with at least two organic nuclei wherein at least one of the multivalent organic nucleus and the organic nuclei is a multicyclic aromatic nucleus.

2. A composition comprising a mixture of non-polymeric compounds characterized in that said mixture (a) is amorphous and (b) is a solid at about 20° C. and (c) comprises at least two different compounds each conforming to the formula

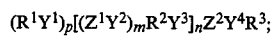

$$(R^1Y^1)_p[(Z^1Y^2)_mR^2Y^3]_nZ^2Y^4R^3;$$

wherein m is zero or one;

n is the number of recurring units in the compound, and is zero up to, but not including, an integer at which said compound starts to become a polymer;

p is an integer of from one to eight;

$R^1$ and $R^3$ each independently represents a monovalent aliphatic or cycloaliphatic hydrocarbon group having 1 to 20 carbon atoms or an aromatic group;

$R^2$, $Z^1$ and $Z^2$ each independently represent multivalent aliphatic or cycloaliphatic hydrocarbon groups having 1 to 20 carbon atoms or an aromatic group;

$Y^1$, $Y^2$, $Y^3$ and $Y^4$ each independently represent a linking group;

provided that at least one of $R^1$, $Z^1$, $R^2$, $Z^2$ and $R^3$ is a multicyclic aromatic nucleus.

3. The composition of claim 2 wherein n is zero;

p is one to eight;

$R^1$ and $R^3$ each independently represent methyl, ethyl, propyl, isopropyl, butyl, hexyl, 2-ethylhexyl, methoxyethyl, ethoxycarbonylpropyl, 3-oxobutyl, 3-thiapentyl, furfuryl, 2-thiazolylmethyl, cyclohexylmethyl, benzyl, phenethyl, phenoxyethyl, vinyl, 2-methylvinyl, pyridyl, phenyl, tolyl, xylyl, naphthyl, anthryl, triptycenyl, p-chlorophenyl, p-nitrophenyl, p-bromophenyl, 2,4-dichlorophenyl, 2-chlorophenyl, 3,5-dinitrophenyl, p-(tetrabromophthalimido)phenyl, p-(tetrachlorophthalimido)phenyl, p-tetraphenylphthalimido)phenyl, p-naphthalimidophenyl, p-(4-nitrophthalimido)phenyl, p-phthalimidophenyl, 1-hydroxy-2-naphthyl, 3,5-dibromo-4-(4-bromobenzoyloxy)phenyl, 3,5-dibromo-4-(3,5-dinitrobenzoyloxy)phenyl or 3,5-dibromo-4-(1-naphthoyloxy)phenyl;

$Z^2$ represents a nucleus derived from 9,9-bis(4-hydroxy-3,5-dichlorophenyl)fluorene; 4,4'-hexahydro-4,7-methanoindan-5-ylidenebis(2,6-dichlorophenol); 9,9-bis(4-hydroxy-3,5-dibromophenyl)fluorene; 4,4'-hexahydro-4,7-methanoindan-5-ylidenebis(2,6-dibromophenol); 3',3'',5',5''-tetrabromophenolphthalein; 9,9-bis(4-aminophenyl)fluorene, phenylindandiol, 1,1'-spirobiindandiol; 1,1'-spirobiindaniamine, 2,2'spirobichroman; 7,7-dimethyl-7H-dibenzo[c,h]xanthenediol; xanthylium salt diols; 9,9-dimethylxanthene-3,6-bis(oxyacetic acid), 4,4'-(3-phenyl-1-indanylidene)diphenol, 3',3'-dibromo-5',5''-dinitro-2',2''-oxaphenolphthalein or 9-phenyl-3-oxo-2,6,7-trihydroxyxanthene; and $Y^1$ and $Y^4$ each independently represents an ester, urethane, amide, imide, nitrilomethyleneoxy, nitrilomethyleneimino, nitrilomethylenethio; 1,3,4-triazol-2,5-ylene or 1,3,4-oxadiazol-2,5-ylene linking group.

4. The mixture of claim 2 wherein at least one of the compounds therein is an oligomer in which
m is one and
n is from one to ten.

5. The mixture of claim 2 selected from the group consisting of

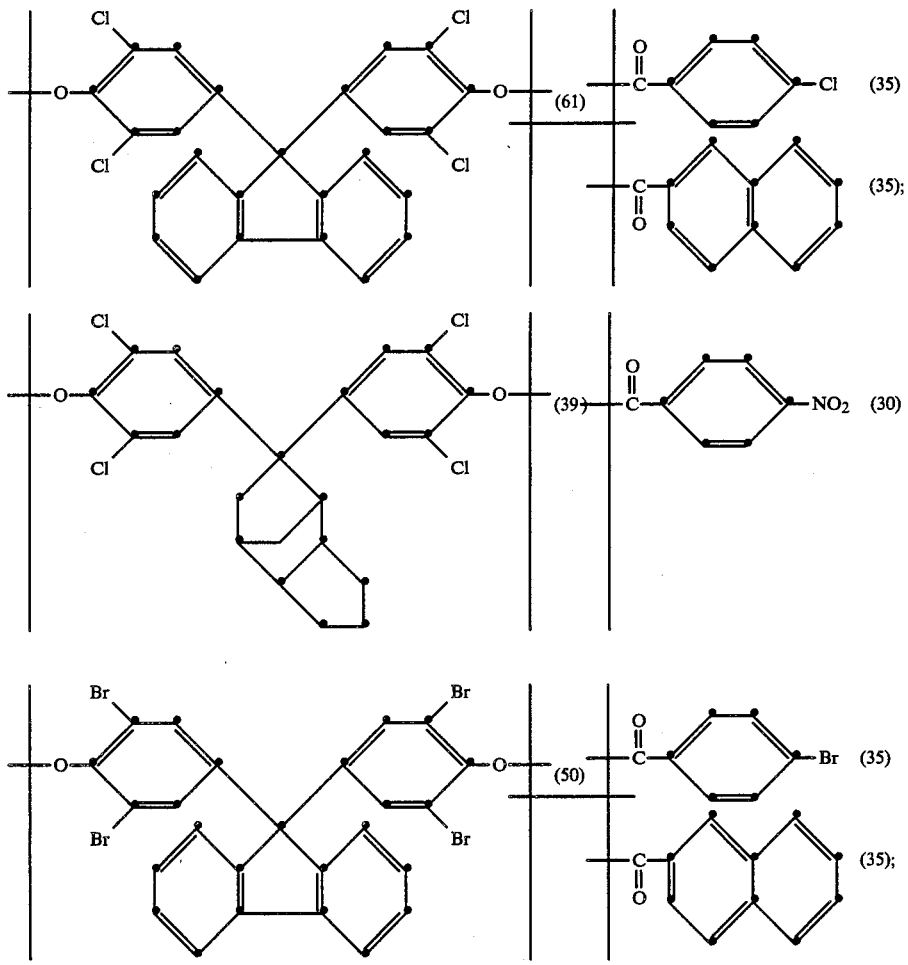

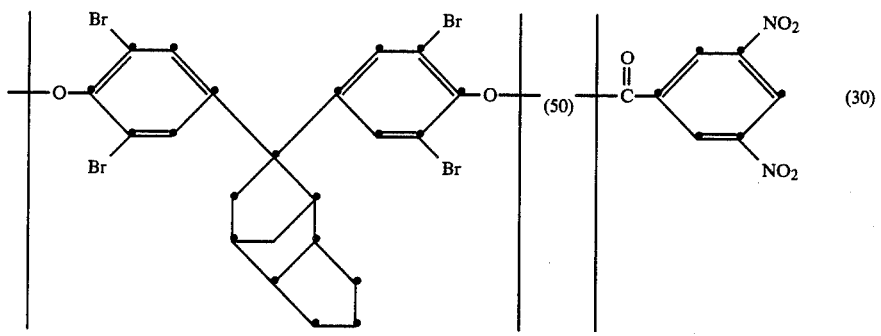
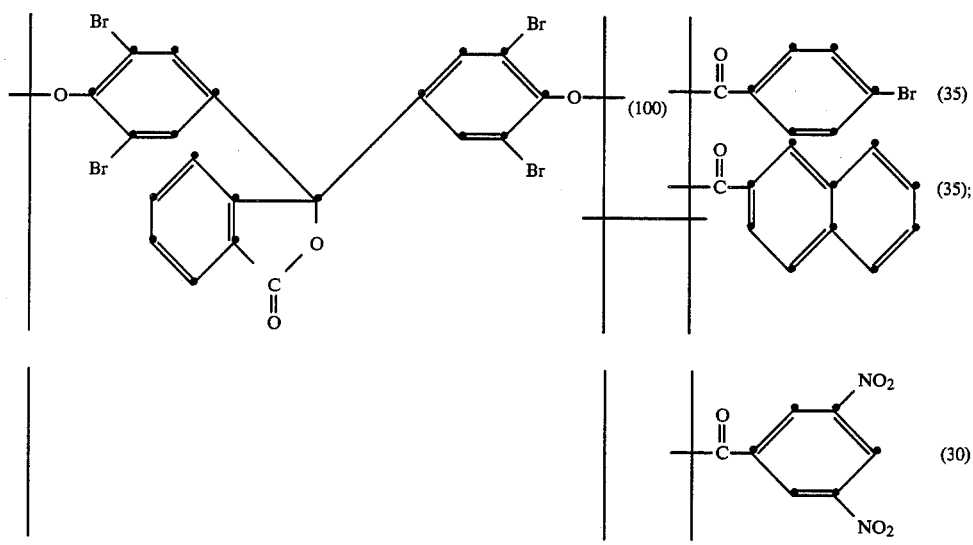
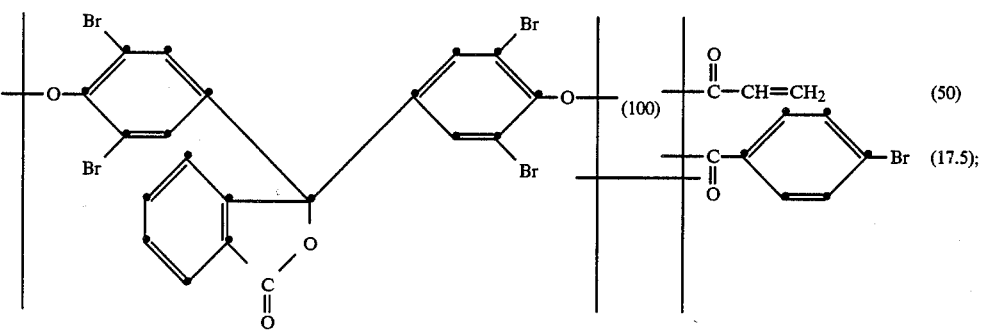
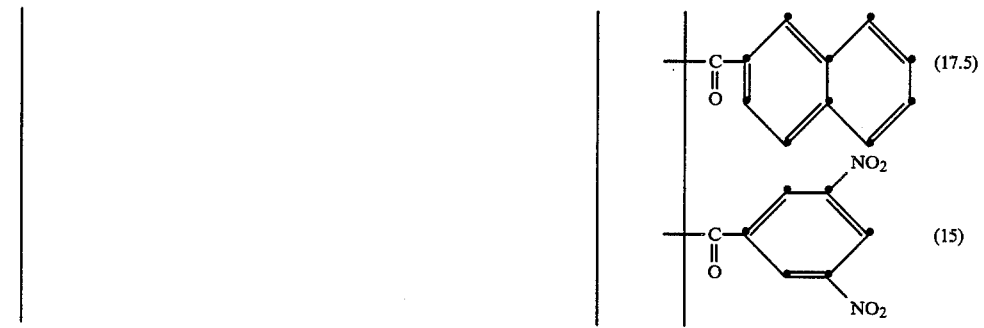

-continued
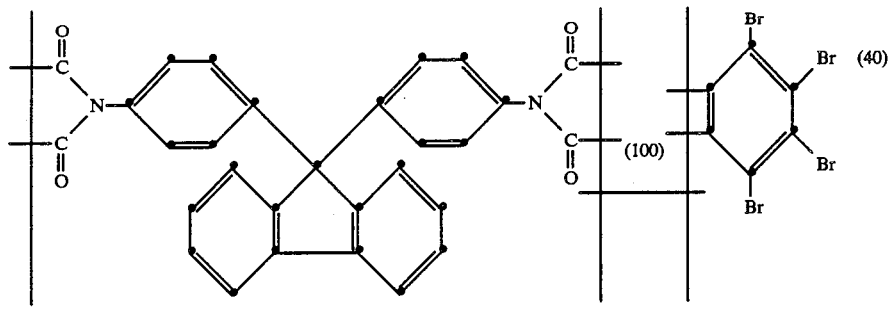
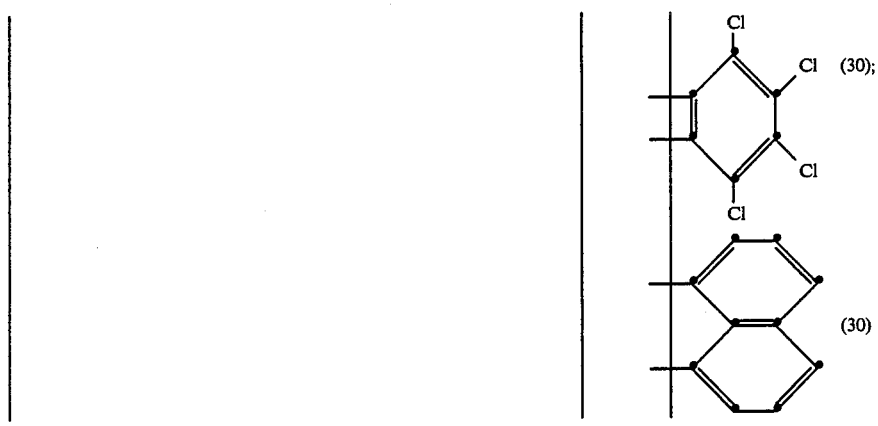
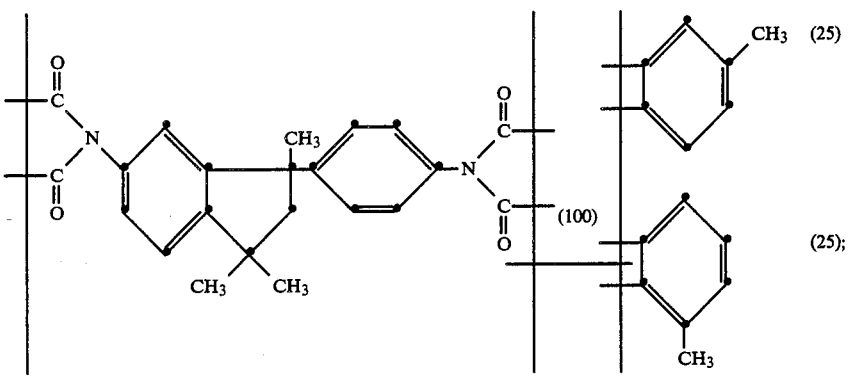
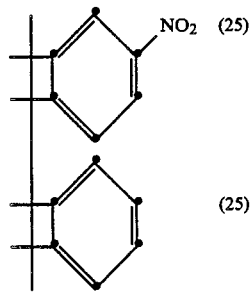

-continued
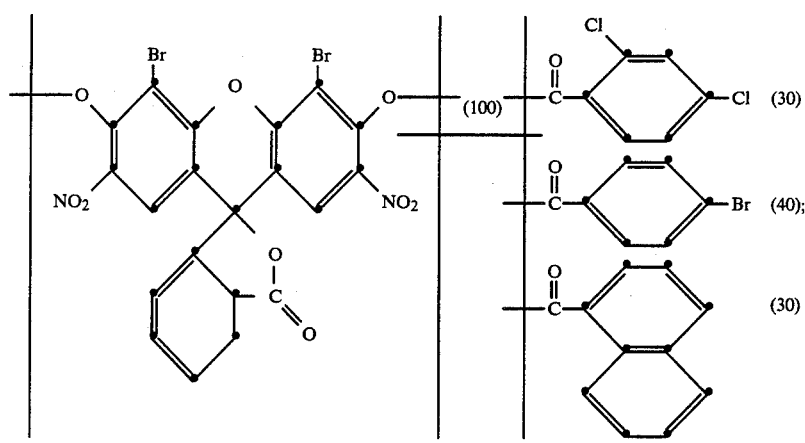
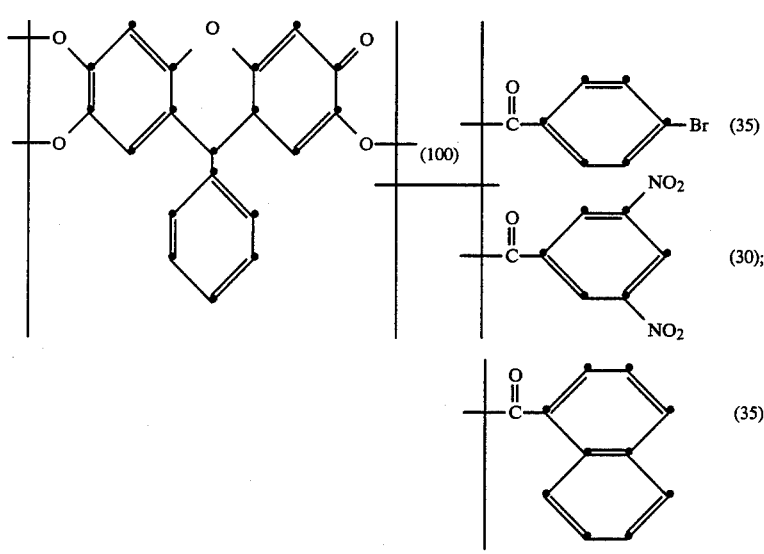
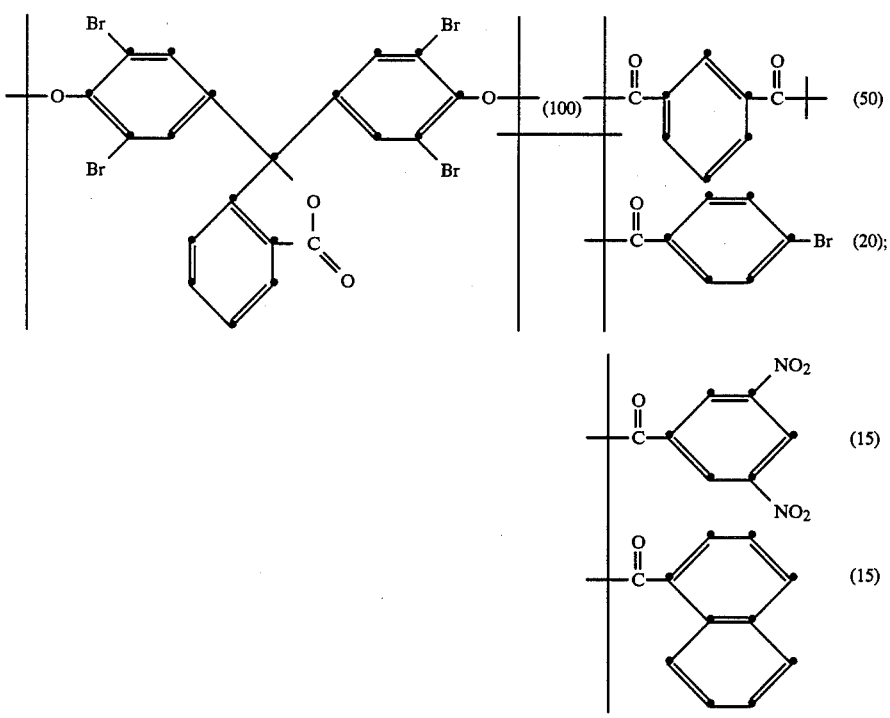

-continued
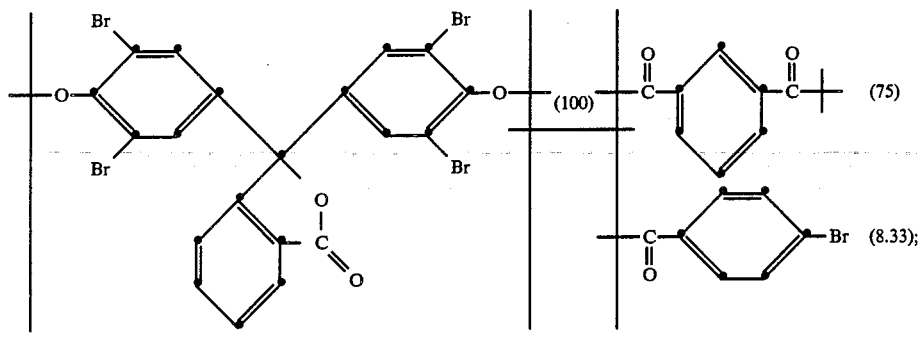
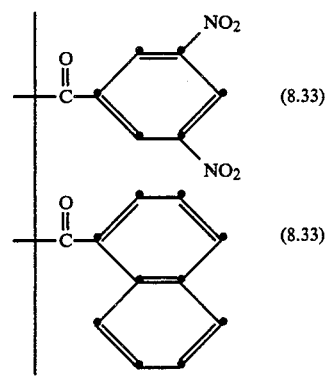
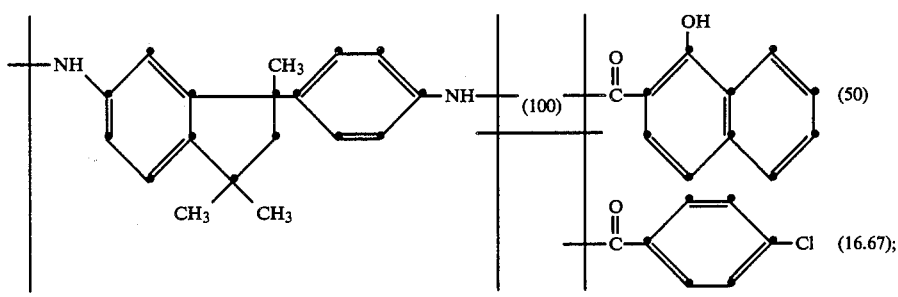
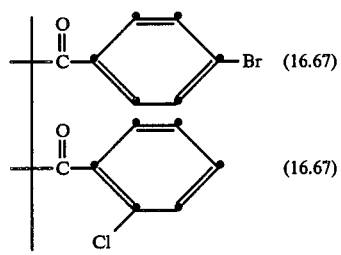

-continued
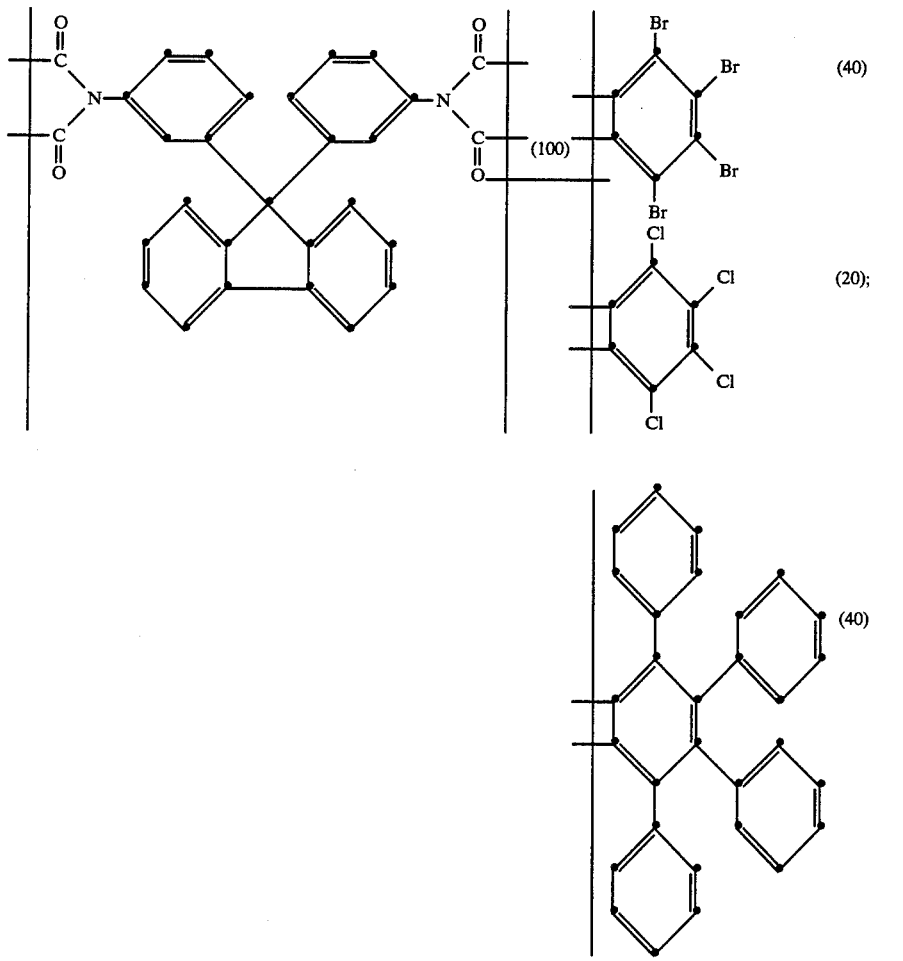
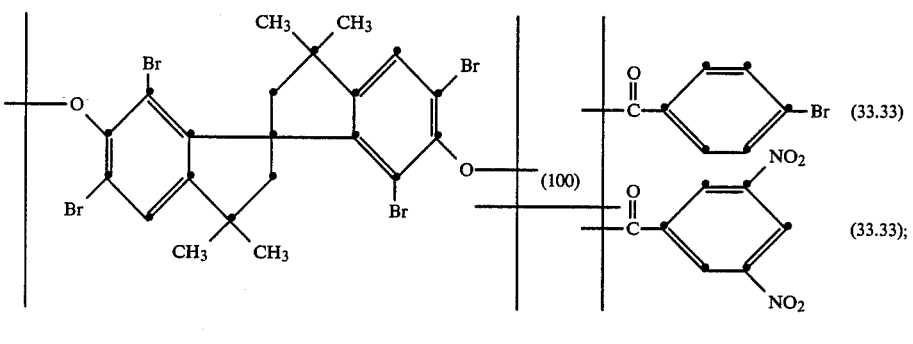
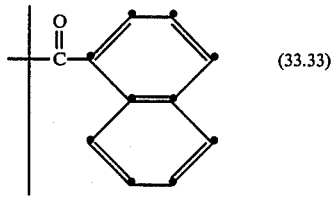

-continued
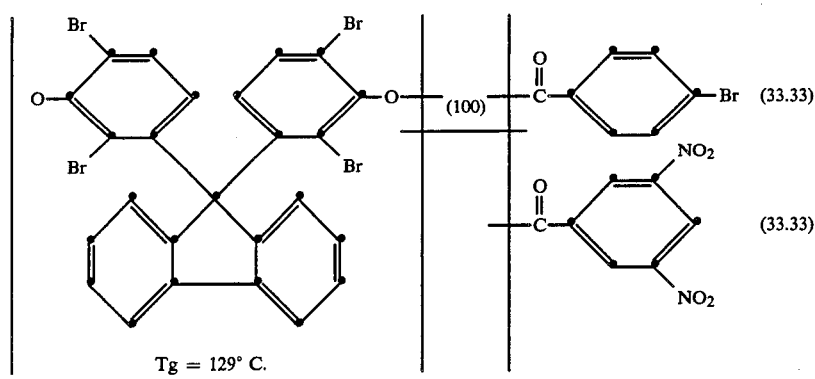
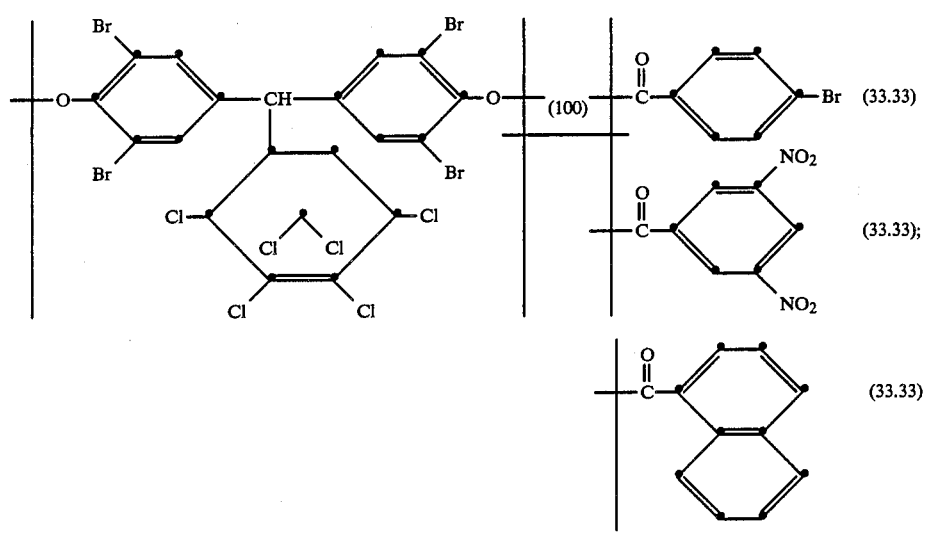
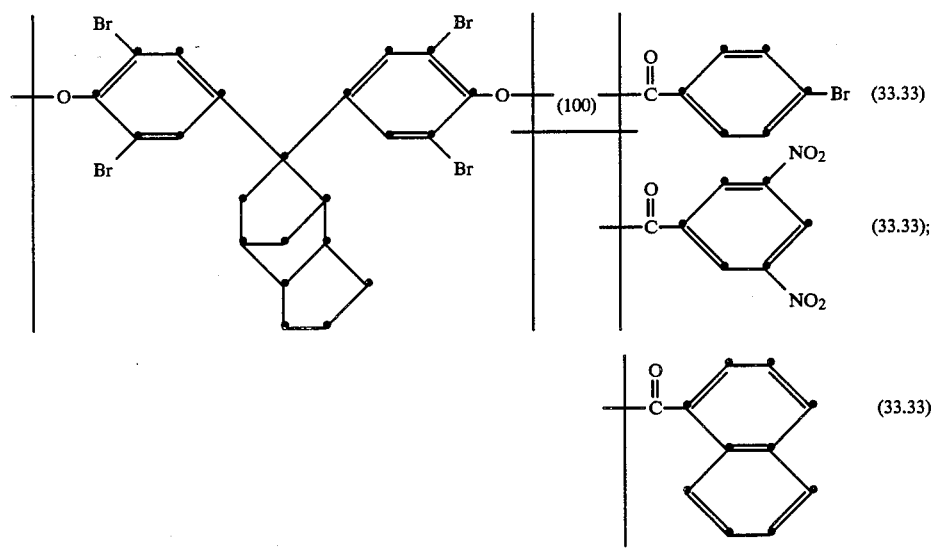

-continued
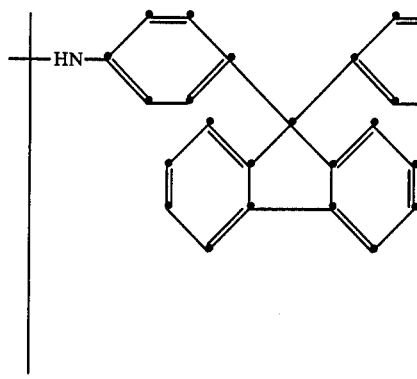 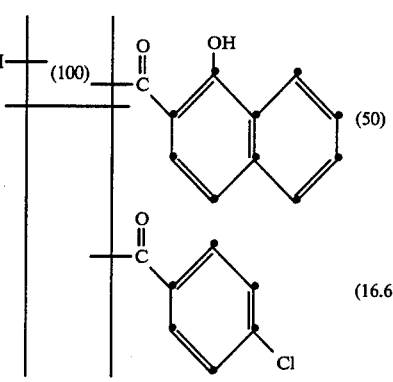
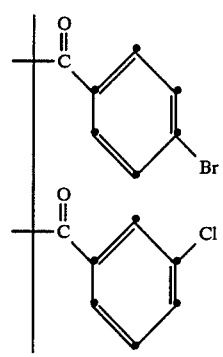
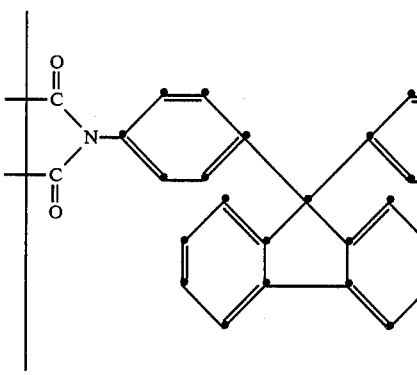 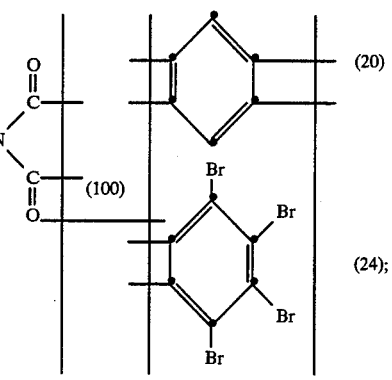
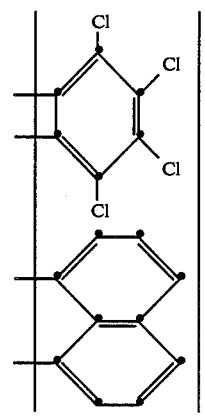

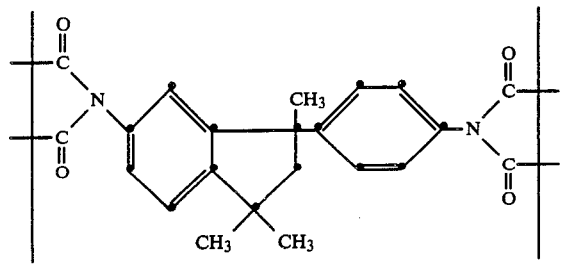
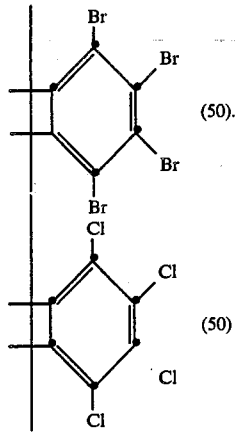
(50).
(50)
6. The mixture of compounds of claim 1, 2, 3, 4 or 5 having a glass transition temperature of at least 100° C.
7. The mixture of compounds of claim 1, 2, 3, 4 or 5 having a glass transition temperature greater than 150° C.
* * * * *